US006287568B1

(12) United States Patent
Wang et al.

(10) Patent No.: US 6,287,568 B1
(45) Date of Patent: Sep. 11, 2001

(54) METHODS RELATING TO IMMUNOGENIC DEXTRAN-PROTEIN CONJUGATES

(75) Inventors: Denong Wang, New York; Bernard F. Erlanger, Whitestone, both of NY (US); Elvin A. Kabat, Falmouth, MA (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/149,997

(22) Filed: Sep. 9, 1998

Related U.S. Application Data
(60) Provisional application No. 60/058,260, filed on Sep. 9, 1997.

(51) Int. Cl.$^7$ ................................................. A01N 65/00
(52) U.S. Cl. ............................. 424/197.11; 424/188.1; 424/208.1; 424/804; 424/812; 530/350; 530/387.5; 530/388.35; 435/329; 435/339.1
(58) Field of Search .................................. 435/329, 330, 435/331, 339, 339.1; 424/184.1, 185.1, 186.1, 187.1, 188.1, 193.1, 194.1, 196.11, 197.11, 204.1, 207.1, 208.1, 804, 812; 530/329, 330, 350, 387.5, 387.7, 387.9, 388.3, 388.35

(56) References Cited

FOREIGN PATENT DOCUMENTS 0 230 222 * 7/1987 (EP).

OTHER PUBLICATIONS

Fernandez et al. "Serum antibody and cellular immune response in mice to dextran B512", Cellular Immunology, vol. 131, No. 1 (Nov. 1990), pp. 41–51. QR185.C4.C4.*
Fujii et al. "Enhancement of systemic and mucosal immune responses following oral administration of liposomes", Immunology Letters, vol. 36, No. 1(Apr. 1993), pp. 65–69. Only the abstract was previously of record.*
Lees et al. "Enhanced immunogenicity of protein–dextran conjugates: I. Rapid stimulation of enhanced antibody responses to poorly immunogenic molecules", Vaccine, vol. 12, No. 13(Oct. 1994), pp. 1160–1166. QR189.V82.*
Agadjanyan, M., et al. (1997) "Peptide mimicry of carbohydrate epitopes on human immunodeficiency virus [see comments]" Nat. Biotechnol., 15:547–551 (Exhibit 2).
Ahonkhai, V.I., et al. (1990) "*Haemophilus influenzae* Type β conjugate vaccine (Meningococcal Protein Conjugate) (PedvaxHIB™):clinical evaluation".
Pediatrics 85, 676–681 (Exhibit 3).
Avrameas, S. (1969) "Coupling of enzyme to proteins with glutaraldehyde" Immunochemistry, 6:42–52 (Exhibit 4).
Barr, N., et al. (1989) "Are pancarcinoma T and Tn differentiation antigens?" (published erratum corrected in Cancer 1989 Oct.) 15;64(8):1594.), Cancer, 64:834–841 (Exhibit 5).

Berek, C. & Ziegner, M. (1993) "Somatic hypermutation and affinity maturation" Immunol. Today, 14:400–404 (Exhibit 6).
Bos, N. A., et al., (1996) "Monoclonal immunoglobulin A derived from peritoneal B cells is encoded by both germ line and somatically mutated V genes and is reactive with commensal bacteria" Infection & Immunity, 64:616–623 (Exhibit 7).
Bos, N. A., et al., (1994) "Analysis of IgA–producing hybridomas derived from peritoneal B1 cells" Advances in Experimental Medicine & Biology, 355:265–269. (Exhibit 8).
Brunswick, M., et al. (1988) "Picogram quantities of anti–Ig antibodies coupled to dextran induce B cell proliferation" J. Immunol., 140:3364–3372 (Exhibit 9).
Campbell, B. J., and V. M. Hirsch (1994) "Extensive envelope heterogeneity of simian immunodeficiency virus in tissues from infected macaques" J. Virol., 68:3129–3137 (Exhibit 10).
Chen, H–T., et al. (1987) "Immunochemical studies on monoclonal antibodies to stearyl–isomaltotetraose from C58/J and a C57BL/10 nude mouse" Mol. Immunol., 24:333–338 (Exhibit 11).
Fernandez, C., and G. Moller (1979) "A thymus–independent IgG response against dextran B512 can be induced in C57BL but not in CBA mice, even though both strains possess a $V_H$dex gene" Scand. J. Immunol., 10:465–472 (Exhibit 12).
Förster, I., and K. Rajewsky (1987) "Expansion and functional activity of Ly–B cells upon transfer of peritoneal cells into allotype–congenic, newborn mice" Eur. J. Immunol., 17:521–528 (Exhibit 13).
Franco, M. A., and H. B. Greenberg (1997) "Immunity to rotavirus in T cell deficient mice" Virology, 238:169–179 (Exhibit deficient mice Virology, 238:169–179 (Exhibit 14).
Haneberg, B., et al. (1994) "Induction of specific immunoglobulin A in the small intestine, colon–rectum, and vagina measured by a new method for collection of secretions from local mucosal surfaces" Infect. Immunol., 62:15–23 (Exhibit 15).

(List continued on next page.)

Primary Examiner—Jeffrey Stucker
(74) Attorney, Agent, or Firm—John P. White; Cooper & Dunham LLP

(57) ABSTRACT

This invention includes the conception of T-independent conjugate-vaccines and its application in the induction of antigen specific IgA response. We demonstrated that 1) α(1,6)dextran can elicit a markedly enhanced IgA response in T-cell free mice (20–50 fold higher than in normal mice); 2)co-injection of the molecule with other antigens can enhance the IgA response to the co-antigen; and 3)a dextran-Gag conjugate can elicit the Gag-specific IgA. Thus, the invention identified α(1,6)dextran as a carrier molecule for producing the T-independent conjugates and as an adjuvant for the enhancement of IgA production. The T-independent property of these conjugates makes it especially useful in vaccinations against HIV and other infectious and non-infectious diseases associated with T-cell deficiency.

41 Claims, 4 Drawing Sheets

OTHER PUBLICATIONS

Haneberg, B., et al. (1995) "The colon and rectum as inductor sites for local and distant mucosal immunity" *Adv. Exp. Med. Biol.*, 371A:107–109 (Exhibit 16).

Hirsch, V. M., et al. (1994) "Spontaneous substitutions in the vicinity of the V3 analog affect cell tropism and pathogenicity of simian immunodeficiency virus" *J. Virol.*, 68:2649–2661. (Exhibit 17).

Ho, D. D., et al. (1995) "Rapid turnover of plasma virions and CD4 lymphocytes in HIV–1 infection" *Nature*, 373:123–126 (Exhibit 18).

Howard, J. (1987) "T cell–independent responses to polysaccharides: their nature and delayed ontogeny". *Towards Better Carbohydrate Vaccines, Proceedings of a meeting organized by the World Health Organization*, Oct. 9–11, 1986, Geneva, pp. 221–231 (Exhibit 19).

Jeanes, A. (1986) "Immunochemical and related interactions with dextrans reviewed in terms of improved structural information" *Mol. Immunol.*, 23:999–1028 (Exhibit 20).

Kabat, E. A., and D. Berg. (1953) "Dextran—an antigen in man" *J. Immunol.*, 70:514–532 (Exhibit 21).

Kabat, E. A. and A. E. Bezer (1958) "The effect of variation in molecular weight on the antigenicity of dextran in man" *Arch. Biochem. Biophys.*, 78:306–318 (Exhibit 22).

Kohler, H., et al. (1992) "Clonal Dominance: Cause for a Limited and Failing Immune Response to HIV–1 Infection and Vaccination" *J. Acq. Imm. Def. Synd.*, 5:1158–1168 (Exhibit 23).

Kraal, G., et al. (1982) "Germinal centre B cells: antigen specificity and changes in heavy class expression" *Nature*, 298:377–379 (Exhibit 24).

Kraehenbuhl, J. P. and M. R. Neutra (1992) "Molecular and cellular basis of immune protection of mucosal surfaces" *Physiological Rev.*, 72(4):853–879 (Exhibit 25).

Kroes, F. G. M., et al. (1990) "Germinal Center Reaction and B Lymphocytes: Morphology and Function" *Curr. Topics Path.*, 84:103–148 (Exhibit 26).

Kroese, F. G., et al. (1995) "Contribution of B–1 cells to intestinal IgA production in the mouse" *Methods*, 8:37–43 (Exhibit 27).

Kwong, P. D., et al. (1998) "Structure of an HIV gp120 envelope glycoprotein in complex with the CD4 receptor and a neutralizing human antibody" *Nature*, 393:648–659 (Exhibit 28).

Madore, D. V., et al. (1990) "Safety and Immunologic Response to *Haemophilus Influenzae* Type b Oligosaccharide–CRM197 Conjugate Vaccine in 1–to 6–Month–Old Infants" *Pediatrics*, 85: 331–337 (Exhibit 29).

Matsuda, T., and E. A. Kabat (1989) "Variable region cDNA sequences and antigen binding specificity of mouse monoclonal antibodies to *isomaltosyl oligosaccharides* coupled to proteins T–dependent analogues of $\alpha(1\rightarrow 6)$ dextran" *J. Immunol.*, 142:863–870 (Exhibit 30).

Mestecky, J., and J. R. McGhee (1987) "Immunoglobulin A (IgA): molecular and cellular interactions involved in IgA biosynthesis and immune response" *Advances in Immunology*, 40:153–245 (Exhibit 31).

Mestecky, J. et al. (1991) "Selective transport of IgA: cellular and molecular aspects" *Gastroenterol. Clin. North Am.*, 20:441–471 (Exhibit 32).

Mestecky, J. (1987) "The common mucosal immune system and current strategies for induction of immune responses in external secretions" *J. Clin. Immunol.*, 7:265–276 (Exhibit 33).

Mombaerts, P., (1994) "Peripheral lymphoid development and function in TCR mutant mice" *Intl. Immunol.*, 6:1061–1070 (Exhibit 34).

Mond, J. J., et al. (1995) "T cell–independent antigens type 2" *Annu. Rev. Immunol.*, 13:655–692 (Exhibit 35).

Nara, P. L., et al. (1991) "Neutralization of HIV–1: a paradox of humoral proportions" *Faseb J.*, 5:2437–2455 (Exhibit 36).

Noorman, F., et al. (1997) "Inhibition of mannose receptor–mediated clearance of tissue–type plasminogen activator (t–PA) by dextran: a new explanation for its antithrombotic effect" *Thromb Haemost.*, 78:1249–1254 (Exhibit 37).

Poussier, P., et al. (1992) "Thymus–independent development and negative selection of T cells expressing T cell receptor $\alpha/\beta$ in the intestinal epithelium: evidence for distinct circulation patterns of gut–and thymus–derived T lymphocytes" *J. Exp. Med.*, 176:187–199 (Exhibit 38).

Rizzuto, C. D., et al. (1998) "A conserved HIV gp120 glycoprotein structure involved in chemokine receptor binding" *Science*, 280:1949–1953 (Exhibit 39).

Robbins, J.B. & Schneerson, R. (1990) "Polysaccharide–Protein Conjugates: A New Generation of Vaccines" *J. Infect. Dis.*, 161: 821–832 (Exhibit 40).

Sabin, A. B. (1992) "Improbability of effective vaccination against human immunodeficiency virus because of its intracellular transmission and rectal poratal of entry" *Proc. Natl. Acad. Sci. USA*, 89:8852–8855 (Exhibit 41).

Sallusto, F., et al. (1995) "Dendritic cells use macropinocytosis and the mannose receptor to concentrate macromolecules in the major histocompatibility complex class II compartment: downregulation by cytokines and bacterial products" *J. Exp. Med.*, 182:389–400 (Exhibit 42).

Schneerson, R., et al. (1987) "Vaccines composed of polysaccharide–protein conjugates: current status,unanswered questions, and prospects for the future" *Towards better carbohydrate vaccines, Proceedings of a meeting organized by the World Health Organization*, Oct. 9–11, 1986, Geneva, pp. 307–332 (Exhibit 43).

Schuler, W., et al. (1984) "Immune response against the T–independent antigen alpha $(1\rightarrow 3)$ dextran, II. Occurrence of B gamma memory cells in the course of immunization with the native polysaccharide is T cell dependent" *Eur. J. Immunol.*, 14:578–585 (Exhibit 44).

Seidl, K. J., et al. (1997) "Frequent occurrence of identical heavy and light chain Ig rearrangements" *Intl. Immunol.*, 9(5) :689–702 (Exhibit 45).

Springer, G. F., et al. (1990) "Pancarcinoma T and Tn epitopes: autoimmunogens and diagnostic markers that reveal incipient carcinomas and help establish prognosis" *Immunodiagnosis of Cancer*, pp. 587–612 (Exhibit 46).

Timens, W., et al. (1989) "Immaturity of the human splenic marginal zone in infancy: possible contribution to the deficient infant immune response" *J. Immunol.*, 143:3200–3206 (Exhibit 47).

Varmus, H. E. (1983) "Retroviruses" *Mobile Genetic Elements*, pp. 411–503 (Exhibit 48).

Van den Eertwegh, et al. (1992) "Complement–mediated follicular localization of T–independent type–2 antigens: the role of marginal zone macrophages revisted" *Eur. J. Immunol.*, 22: 719–726 (Exhibit 49).

Wang, D., et al. (1991) "The Repertoire of Antibodies to a Single Antigenic Determinant" *Mol. Immunol.*, 28(12):1387–1397 (Exhibit 50).

Wang, D., et al. (1994) "Reaction of germinal centers in the T–cell–independent response to the bacterial polysaccharide α(1→6)dextran" *Proc. Natl. Acad. Sci. USA*, 91:2502–2506 (Exhibit 51).

Wang, D., Stall, A.M. & Kabat E.A. "B Cell Responses to α(1→6) dextran in T Cell Deficient Mice" *The 9th International Congress of Immunology* (*ed. AAI*), Abstract #: 3054 (San Francisco, California, 1995) (Exhibit 52).

Wang, D. & Kabat, E. A., (1998) "Antibodies, Specificity" *Encyclopedia of Immunology*, Academic Press Ltd (2d Ed) pp. 1–6 (Exhibit 53).

Wang, D., et al. (1993) "Modeling Study of Antibody Combining Sites to α(1→6)dextrans" *J. Biol. Chem.* 268(27) 20584–20589 (Exhibit 54).*

Wang, D. & Kabat, E.A. (1996) "Carbohydrate Antigens (Polysaccharides)" *Structure of Antigens*, CRC Press, Inc., vol. 3, pp. 247–276 (Exhibit 55).*

Wei, X. et al. (1995) "Viral dynamics in human immunodeficiency virus type 1 infection" *Nature*, 373:117–122 (Exhibit 56).*

Wyatt, R., et al. (1998) "The antigenic structure of the HIV gp120 envelope glycoprotein" *Nature*, 393:705–711, (Exhibit 57).*

* cited by examiner

α(1,6)Dextran induced markedly enhanced IgA response in TCR β/δ KO mice of the C57BL backgroung.

Co-sitimulation with α(1,6)Dex, the B1355S-specific IgA response was extensively enhanced in KO mice.

Boosting or primary immunization using the CAD conjugate modulates the isotype profile of responding B-cells: enhanceme of IgA and κ isotypes GK: Gag-KLH conjugate; GAD: Gag-dextan conjugate; KO: C57BL (TCRβ/δ Knock-out)

METHODS RELATING TO IMMUNOGENIC DEXTRAN-PROTEIN CONJUGATES

This application claims the benefit of U.S. provisional application No. 60/058,260, filed Sep. 9, 1997, the contents of which is hereby incorporated by reference.

Throughout this application, various references are referred to with arabic numbers. Disclosures of these publications in their entireties are hereby incorporated by reference into this application to more fully describe the state of the art to which this invention pertains. Full bibliographic citation for these references may be found at the end of this specification, preceding the claims.

BACKGROUND OF THE INVENTION

Recognition of polysaccharides as antigens began with the study in 1917 by Dochez and Avery(1) who found that when pneumococci are grown in fluid media, there is a substance in the culture fluid which precipitated specifically with antisera to the same pneumococcus. Heidelberger and Avery(2) showed that this substance was polysaccharide and not protein as thought previously.

Microbial polysaccharides as antigens gained renewed interest when it was found that strains of microorganisms resistant to antibiotics and/or chemotherapeutic agents appeared increasingly and became a worldwide problem. Vaccines with microbial polysaccharides were developed to meet the requirements.

Given the feature of host immune responses induced by polysaccharides, they were classified as the "T-independent" (TI) antigen. The concept of T-independency arose from the observations that neonatally thymectomized (3,4) and nude mice(5) gave unimpaired antibody responses to large polymeric molecules, although they were not able to mount a humoral response to T-dependent (TD) antigens, such as proteins. They are further divided into type I(TI-I) and type II(TI-II), based on the ability to elicit antibodies in the CBA/N mouse strain, with an X-chromosome linked immunodeficiency (xid) (6). Lipopolysaccharides (LPS) of gram-negative bacteria which induce antibodies in such strains are TI-I antigens; capsular polysaccharides of gram positive bacteria and exopolysaccharides, induced no response in xid strains, are TI-II antigens.

T-dependent and T-independent antigens may induce different pathways of B cell activation and differentiation, germinal center reactions and antibody-secreting cell responses. T-dependent antigens can induce germinal center formation as well as the antibody-secreting cell responses. In germinal centers, B cells may undergo somatic hypermutation, IgH class-switching and memory cell induction(7–9). These molecular events are believed to be T cell dependent. In contrast to the T-dependent patterns of B cell activation which are associated with germinal center development, many T-independent antigens, such as the TI-I antigen LPS and the TI-II antigens, polyvinylpyrrolidone and DNP-Ficoll, are reported to induce only minimal or no germinal center development (72).

The onset of full response to polysaccharide TI-II antigens in both mice and humans is strikingly delayed. In mice(10) antibody responses to TI-I antigens(LPS and other) and protein antigens reach adult levels within 1–2 weeks; antibodies to TI-II antigens can be detected only at 2–3 weeks. For pneumococcal polysaccharides SSS-III and dextran B1355S, full development of the antibody response is not reached until 4 weeks; with levan and α(1,6)dextran, 7 and 13 weeks respectively, are needed. In humans, children younger than 18 months of age fail to respond to microbial polysaccharides or produce antibodies at levels too low to be protective. Such poor responsiveness generally lasts until 5 years of age. Thus, there is a period when maternal-derived protective antibodies have declined, yet the age-related development of immunity to bacterial infection remains immature. Pathogens causing severe problems during this high-risk period have long posed the need for developing efficient vaccines.

Thus, the "T-independent" property of polysaccharide antigens has been considered as a limitation to their application for vaccination. In 1990, Robbins and Schneerson introduced a conjugate strategy for vaccine development (11). By coupling purified capsular polysaccharides of *Haemophilus influenzae* B with tetanus toxoid, the first polysaccharide-protein conjugate against this bacterium was made(12). Instead of large capsular polysaccharides, its oligosaccharide was conjugated with different protein carriers for vaccinations (13,14), so that the conjugate-vaccines preserve the antigenic specificities of the original polysaccharides but gain the T-dependent property in addition. A significant shift in the age at which the anti-carbohydrate response can be induced and Ig class switches to the protective IgG isotypes were observed with these vaccines, resulting in better protection of high-risk populations from *Haemophilus influenzae* B. The principles underlying the approaches to *Haemophilus influenzae* B vaccines, have been extended to microbial polysaccharides of other bacteria, viruses and parasites, etc.(15).

The magnitude of the worldwide AIDS epidemic presents current challenges for developing effective vaccines and therapeutic strategies These efforts are hampered, however, by the targeted elimination of T-cells by the retrovirus(16, 17), by difficulties in inducing effective neutralizing antibodies to HIV1(7–19), and by the lack of an effective strategy for the induction of mucosal immune response, which may eliminate the invasion on the mucosal surface before a systemic infection occurs. The center of the difficulties in developing HIV-vaccines is a paradox caused by the retrovirus: effective vaccinations require the functions of T-cell which are however destroyed directly by the virus.

An effective vaccination against HIV must fulfill the following requirements: 1) It must elicit an effective immune response to HIV in the presence and absence of functional T-cells; 2) It can induce anti-HIV antibody of the IgA isotype to enhance the mucosal protection; and 3) It is safe, non-toxic and clinically acceptable. In addition, a vaccination strategy applying such T-independent Vaccines must be able to inherit all the advantages of the current T-dependent "conjugate-vaccines".

Our invention described here provides the concept, materials and the methodology for the development of such vaccination strategies against HIV, and other infectious agents.

SUMMARY OF THE INVENTION

This invention includes the conception of the T-independent conjugate-vaccines, their application in the induction of antigen specific IgA and in reshaping the repertoire of responding B-cells. We demonstrated for the first time that a specific polysaccharide antigen α(1,6) dextran can elicit a markedly enhanced IgA response in T-cell free mice; co-injection of the molecule with other antigens can enhance the IgA response to the co-antigen; and its conjugates with the Gag protein of HIV-1 can elicit Gag-specific IgA in the presence and absence of functional T-cells.

The invention identified and illustrated specifically: 1. α(1,6)dextran can serve as a carrier molecule for producing the T-independent conjugate-vaccines; 2. The polysaccharide can serve as an adjuvant to enhance IgA production for other specificities and to reshape the repertoire of responding B-cells; 3. The technical details for producing the first generation of the TI-conjugate-vaccines and their in vitro identification are described; and 4. A combinatory vaccination strategy, incorporating the advantage of both "TD-conjugate" and our "TI-conjugates", is proposed and experimentally illustrated.

The T-independent property of these conjugates makes it especially useful in vaccinations against HIV, AIDS-associated opportunistic infections, and other infectious- and non-infectious diseases with T-cell deficiency (including tumors). Its application is, however, not restricted in the T-cell deficient situation.

This invention provides a method of identifying an α(1,6) dextran molecule as a potent IgA-B cell activator comprising the steps of:

(a) conjugating a first and a second α(1,6) dextran molecule, each molecule having a different molecular weight of $\geq 90$ kd, to an HIV-1 gp120 glycoprotein, an HIV-1 protein or epitopes thereof to produce a T-independent α(1,6) dextran conjugate;

(b) administering the first T-independent α(1,6) dextran conjugate produced in step (a) to a subject to induce anti-HIV-1 gp12o antibodies in the subject;

(c) detecting an amount of anti-HIV-1 gp120 antibodies induced in step (b) in the subject;

(d) administering the second T-independent α(1,6) dextran conjugate produced in step (a) to a subject to induce anti-HIV-1 gp120 antibodies in the subject;

(e) detecting an amount of anti-HIV-1 gp120 antibodies induced in step (d) in the subject;

(f) comparing the amount of anti-HIV-1 gp120 antibodies detected in step (c) to the amount of anti-HIV-1 gp120 antibodies detected in step (e), wherein detection of a greater amount of anti-HIV-1 gp120 antibodies induced by the first or second α(1,6) dextran molecule identifies the a(1,6) dextran molecule which is a potent IgA-B cell activator.

In another embodiment of the method, the HIV-1 gp120 glycoprotein is a deglycosylated wildtype HIV-1 gp120 glycoprotein or a deletion form of the deglycosylated wildtype HIV-1 gp120 glycoprotein.

In a further embodiment of the method, the deglycosylated wildtype HIV-1 gp120 glycoprotein or the deletion form of the deglycosylated wildtype HIV-1 gp120 glycoprotein binds CD4 or an HIV-1 co-receptor.

In a further embodiment of the method the HIV-1 co-receptor

This invention also provides a method of inducing antigen specific antibodies in an immunocompromised subject, wherein the antigen comprises an epitope of HIV-1 gp120 glycoprotein an or an HIV-1 gp120 protein, comprising administering an effective amount of a T-independent α(1,6)dextran conjugate to the immunocompromised subject.

This invention also provides a method of enhancing IgA response in an immunocompromised subject comprising administering α(1,6)dextran having a molecular weight of $\prec 90$ kd and an effective amount of an antigen concurrently.

This invention also provides a method of treating an immunocompromised subject comprising the method of inducing antigen specific antibodies in an immunocompromised subject, wherein the antigen comprises an epitope of HIV-1 gp120 glycoprotein an or an HIV-1 gp120 protein, comprising administering an effective amount of a T-independent α(1,6)dextran conjugate to the immunocompromised subject.

This invention also provides a method of treating an immunocompromised subject comprising a method of enhancing IgA response in an immunocompromised subject comprising administering α(1,6)dextran having a molecular weight of $\prec 90$ kd and an effective amount of an antigen concurrently.

This invention also provides a method of preventing AIDS or HIV-1 infection in a subject comprising the method of inducing antigen specific antibodies in an immunocompromised subject, wherein the antigen comprises an epitope of HIV-1 gp120 glycoprotein an or an HIV-1 gp120 protein, comprising administering an effective amount of a T-independent α(1,6)dextran conjugate to the immunocompromised subject.

This invention also provides a method of preventing AIDS or HIV-1 infection in a subject comprising a method of enhancing IgA response in an immunocompromised subject comprising administering α(1,6)dextran having a molecular weight of $\prec 90$ kd and an effective amount of an antigen concurrently.

This invention also provides a method of producing a T-independent conjugate comprising conjugating a microbial antigen protein or an epitope thereof to α(1,6) dextran.

This invention also provides a method of inducing antigen specific IgA in a subject, wherein the antigen is a microbial protein, carbohydrate or a fragment thereof comprising administering a therapeutically effective amount of the T-independent conjugate vaccine produced by a method of producing a T-independent conjugate comprising conjugating a microbial antigen protein or an epitope thereof to α(1,6) dextran to the subject.

This invention also provides a method of inducing antigen specific IgA in a subject, wherein the antigen is a microbial antigen or epitope thereof comprising administering α(1,6) dextran and an effective amount of an antigen sequentially or concurrently.

In an embodiment of either of the above-described methods the subject is T-cell deficient.

In an embodiment of the method of either of the above-described methods of inducing antigen specific IgA the subject is not T-cell deficient.

This invention further provides a method of treating a microbial infection in a subject comprising the method inducing antigen specific IgA in a subject, wherein the antigen is a bacterial envelope protein or a fragment thereof comprising administering a therapeutically effective amount of the T-independent conjugate vaccine produced by a method of producing a T-independent conjugate comprising conjugating a microbial antigen protein or an epitope thereof to α(1,6) dextran to the subject.

This invention also provides a method of treating a microbial infection in a subject comprising the method of inducing antigen specific IgA in a subject, wherein the antigen is a microbial antigen or epitope thereof comprising administering α(1,6)dextran and an effective amount of an antigen sequentially or concurrently.

This invention further provides a method of preventing a microbial infection in a subject comprising the method of inducing antigen specific IgA in a subject, wherein the antigen is a bacterial envelope protein or a fragment thereof comprising administering a therapeutically effective amount of the T-independent conjugate vaccine produced by a method of producing a T-independent conjugate comprising conjugating a microbial antigen protein or an epitope thereof to α(1,6) dextran to the subject.

This invention further provides a method of preventing a microbial infection in a subject comprising the method of inducing antigen specific IgA in a subject, wherein the antigen is a microbial antigen or epitope thereof comprising administering α(1,6)dextran and an effective amount of an antigen sequentially or concurrently.

This invention also provides a composition comprising a T-independent conjugate in an amount effective to induce antigen specific IgA in a subject and a pharmaceutically acceptable carrier.

This invention also provides a method of producing a composition comprising a T-independent conjugate in an amount effective to induce antigen specific IgA in a subject and a pharmaceutically acceptable carrier comprising the the above-described method identifying an α(1,6) dextran molecule as a potent IgA-B cell activator and further comprising admixing the T-independent conjugate and the pharmaceutically acceptable carrier.

A composition comprising an effective amount of a T-independent conjugate and a pharmaceutically acceptable carrier, wherein the T-independent conjugate is produced by the the above-described method of identifying an α(1,6) dextran molecule as a potent IgA-B cell activator.

This invention provides a composition comprising a effective amount of a T-independent conjugate and a pharmaceutically acceptable carrier, wherein the T-independent conjugate is produced by the method of producing a T-independent conjugate comprising conjugating a microbial antigen protein or an epitope thereof to α(1,6) dextran.

This invention also provides the use of the α(1,6) dextran molecule identified as a potent antibody activator by the above-described method as a carrier or an adjuvant for vaccines to enhance mucosal immunity.

In an embodiment of the above described method the T-independent conjugate is used as a vaccine to induce antigen specific IgA.

DETAILED DESCRIPTION OF THE INVENTION

Figure 1:
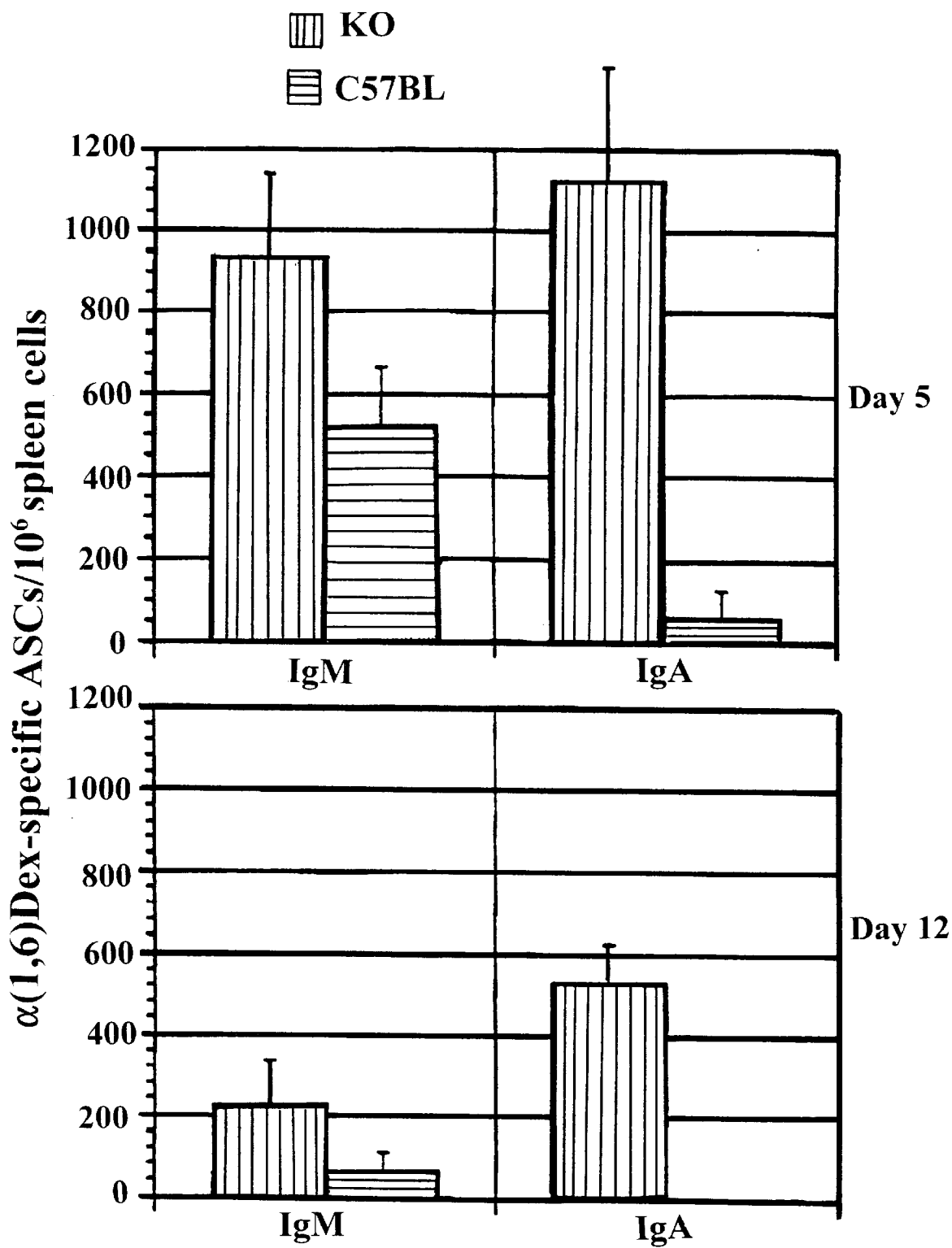
FIG. 1: Demonstrates the first time the strikingly enhanced IgA response to α(1,6)dextran by a strain of T-cell free mice, C57BL(TCR β/δ genes knock-out), which has been back-crossed to the C57BL background. TCR β/δ KO mice and C57BL controls were both immunized i.v. with 10 μg of α(1,6)dextran, N279, and at the indicated times spleen cells were isolated and the number of antigen specific ASC was determined by antigen-specific ELISA-spot assay. The specificity of ELISA-spots was established by competitive blocking with α(1,6)dextran, N279, but not by α(1,3)α(1, 6)dextran, B1355S. Six to ten animals were tested at each time point. ASC stands for antibody secreting cell. Data were expressed as the number of N279 specific ASC per $10^6$ splenocytes. IgA response to α(1,6)dextran is enhanced in a strain of T-cell free mice of C57Bl background. this is consistent with our previous observation in the KO mice of mix background (129XC57BL/6J). β/δ KO mice and C57BL controls were both immunized i.v. with 10 μg of α(1→6) dextran, N279, and at the indicated times spleen cells were isolated and the number of antigen specific ELISA-spot assay. The specificity of ELISA-spots was established by competitive blocking with α(1→6)dextran, N279, but not by α(1→3)α(1→6)dextran, B1355S. Six to ten animals were tested at each time point. Data are expressed as the number of N279 specific ASC per $10^6$ splenocytes.

This invention provides a method of identifying an α(1,6) dextran molecule as a potent IgA-B cell activator comprising the steps of:

(a) conjugating a first and a second α(1,6) dextran molecule, each molecule having a different molecular weight of ≧90 kd, to an HIV-1 gp120 glycoprotein, an HIV-1 protein or epitopes thereof to produce a T-independent α(1,6) dextran conjugate;

(b) administering the first T-independent α(1,6) dextran conjugate produced in step (a) to a subject to induce anti-HIV-1 gp120 antibodies in the subject;

(c) detecting an amount of anti-HIV-1 gp120 antibodies induced in step (b) in the subject;

(d) administering the second T-independent α(1,6) dextran conjugate produced in step (a) to a subject to induce anti-HIV-1 gp120 antibodies in the subject;

(e) detecting an amount of anti-HIV-1 gp120 antibodies induced in step (d) in the subject;

(f) comparing the amount of anti-HIV-1 gp120 antibodies detected in step (c) to the amount of anti-HIV-1 gp120 antibodies detected in step (e), wherein detection of a greater amount of anti-HIV-1 gp120 antibodies induced by the first or second α(1,6) dextran molecule identifies the α(1,6) dextran molecule which is a potent IgA-B cell activator.

In an embodiment of the above-described method, the induced anti-HIV-1 gp120 antibodies are IgA antibodies or IgG antibodies.

In another embodiment of the method, the HIV-1 gp120 glycoprotein is a deglycosylated wildtype HIV-1 gp120 glycoprotein or a deletion form of the deglycosylated wildtype HIV-1 gp120 glycoprotein. In a further embodiment of the method, the deglycosylated wildtype HIV-1 gp12o glycoprotein or the deletion form of the deglycosylated wildtype HIV-1 gp120 glycoprotein binds CD4 or an HIV-1 co-receptor.

In a further embodiment of the method the HIV-1 co-receptor is HIV-1 coreceptor CCR5 or CXCR4.

In a further embodiment of the method, the deletion form of the deglycosylated wildtype HIV-1 gp120 glycoprotein has domains $v_1$ and $v_2$ deleted from the deglycosylated wildtype HIV-1 gp120 glycoprotein.

In a further embodiment of the above-described method, in step (a) the α(1,6) dextran molecule is conjugated to the HIV-1 gp120 glycoprotein or an epitope thereof, by a heteroligation technique.

In a further embodiment of the above-described method, the HIV-1 gp120 protein epitope is a carbohydrate epitope.

In a further embodiment of the method, the carbohydrate epitope is coupled to a lipid carrier and incorporated into the surface of a liposome carrier.

In a further embodiment of the method, an additional carbohydrate epitope is incorporated into the liposome, wherein the carbohydrate epitope comprises an isomaltosyl oligosaccharide.

In a further embodiment of the method, the isomaltosyl oligosaccharide comprises a [Glc(α(1,6)]$_n$ motif.

In a further embodiment of the method, the HIV-1 gp120 protein or an epitope thereof is biotinylated and is conjugated to the α(1,6) dextran which is biotinylated by avidin.

In a further embodiment of the method, the HIV-1 gp120 glycoprotein epitope is Tn (GalNAc-Ser/Thr), Lewis Y (Fucα1→2Galβ1→4 (Fucα1→3) GlcNAcβ1→3Galβ1→4Glcβ1→R) or peptide mimics thereof.

In a further embodiment of the method, the HIV-1 protein is a Gag p55 polyprotein or a capsid p24 protein.

In a further embodiment of the method, the Gag is a Gag-GST fusion protein or a purified Gag protein.

This invention also provides a method of inducing antigen specific antibodies in an immunocompromised subject, wherein the antigen comprises an epitope of HIV-1 gp120 glycoprotein an or an HIV-1 gp120 protein, comprising administering an effective amount of a T-independent α(1,6)dextran conjugate to the immunocompromised subject.

In another embodiment of the above-described method, the antibodies are IgA antibodies or IgG antibodies.

As defined herein an effective amount of a T-independent α(1,6)dextran conjugate is an amount of the conjugate that induces HIV-1 neutralization antibodies of IgA and/or IgG isotypes in the circulation of a subject and/or at mucosal sites of the body of the subject. HIV-1 neutralization antibodies are antibodies which specifically bind to the HIV neutralization epitopes such as the CD4-binding region or those regions interacting with an HIV coreceptor, such as CCR5 so as to block infection by HIV-1.

In a further embodiment of the method, the T-independent α(1,6)dextran conjugate comprises an α(1,6)dextran and a protein coupled thereto.

In a further embodiment of the method, the protein is HIV-1 gp120 glycoprotein, deglycosylated wildtype HIV-1 gp120 glycoprotein or the deletion form of the deglycosylated wildtype HIV-1 gp120 glycoprotein.

In a further embodiment of the method, the deletion form of the deglycosylated wildtype HIV-1 gp120 glycoprotein has domains $v_1$ and $v_2$ deleted from the deglycosylated wildtype HIV-1 gp120 glycoprotein.

In a further embodiment of the method, the T-independent α(1,6)dextran conjugate comprises gp120, a deletion form of gp120 wildtype, a deglycosylated gp120 or a deletion form of deglycosylated gp120.

In a further embodiment of the method, the T-independent α(1,6)dextran conjugate is DEX-LeY-peptide.

In a further embodiment of the method, the epitope of gp120 glycoprotein is a carbohydrate molecule.

In a further embodiment of the method, the carbohydrate molecule is Tn (GalNAc-Ser/Thr).

In a further embodiment of the method, the carbohydrate molecule is a peptide mimic of a mucin-type structure or of a peripheral poly-N-acetyl-glucosamine carbohydrate structure.

In a further embodiment of the method, the carbohydrate mimicking peptide is YPY that mimics mannose or WRY that mimics (α(1,→4) glucose.

In a further embodiment of the method, the carbohydrate molecule is Lewis Y (Fucα1→2Galβ1→4 (Fucα1→3) GlcNAcβ1→3Galβ1→4Glcβ1→R).

In a further embodiment of the method, the epitope is a peptide mimic of Lewis Y.

In a further embodiment of the method, the peptide mimic of Lewis Y comprises the amino acid sequence YYRYD (SEQ ID NO: 1) or YYRYDK (SEQ ID NO: 2).

In a further embodiment of the method, the induced antigen specific antibodies are IgA antibodies or IgG antibodies in the circulation of the subject or at mucosal sites of the subject.

In a further embodiment of the method, the induced mucosal IgA antibodies are colo-rectal, genital, or oral IgA antibodies.

In a further embodiment of the method, the immunocompromised subject is infected with human immunodeficiency virus-1 (HIV-1).

In a further embodiment of the method, the subject is T-cell deficient.

As used herein T cell deficiency is defined as CD4 counts of between 200 and 500 cells/m$^3$ or lower than 200 cells/mm$^3$.

In a further embodiment of the method, the subject is not T-cell deficient.

In a further embodiment of the method, the T-independent α(1,6)dextran conjugate is administered to a mucosal surface of the immunocompromised subject or via a systemic route of vaccination.

In a further embodiment of the method, the administration is topical, oral, nasal, anal, liposome-mediated delivery, aerosol delivery, intravenous delivery or subcutaneous delivery.

This invention also provides a method of enhancing IgA response in an immunocompromised subject comprising administering α(1,6)dextran having a molecular weight of −<90 kd and an effective amount of an antigen concurrently.

In a further embodiment of the method, the subject is T-cell deficient.

In a further embodiment of the method, the subject is not T-cell deficient.

In a further embodiment of the method, the antigen comprises an HIV-1 gp120 glycoprotein, or other HIV-1 proteins or epitopes derived from HIV proteins.

In a further embodiment of the method, the HIV-1 gp120 glycoprotein is deglycosylated wildtypeD gp120 protein.

In a further embodiment of the method, the deglycosylated wildtype HIV-1 gp120 glycoprotein is a deletion form of the deglycosylated wildtype HIV-1 gp120 glycoprotein having deletions of domains $v_1$ and $v_2$.

In a further embodiment of the method, the HIV-1 gp120 glycoprotein epitope is Tn (GalNAc-Ser/Thr), Lewis Y (Fucα1→2Galβ1→4) (Fucα1→3) GlcNAcβ1→3Galβ1→4Glcβ1→R) or peptide mimics thereof.

This invention also provides a method of treating an immunocompromised subject comprising the method of inducing antigen specific antibodies in an immunocompromised subject, wherein the antigen comprises an epitope of HIV-1 gp120 glycoprotein or an HIV-1 gp120 protein, comprising administering an effective amount of a T-independent α(1,6)dextran conjugate to the immunocompromised subject.

This invention also provides a method of treating an immunocompromised subject comprising a method of enhancing IgA response in an immunocompromised subject comprising administering α(1,6)dextran having a molecular weight of −<90 kd and an effective amount of an antigen concurrently.

This invention also provides a method of preventing AIDS or HIV-1 infection in a subject comprising the method of inducing antigen specific antibodies in an immunocompromised subject, wherein the antigen comprises an epitope of HIV-1 gp120 glycoprotein or an HIV-1 gp120 protein, comprising administering an effective amount of a T-independent α(1,6)dextran conjugate to the immunocompromised subject.

This invention also provides a method of preventing AIDS or HIV-1 infection in a subject comprising a method of enhancing IgA response in an immunocompromised subject comprising administering α(1,6)dextran having a molecular weight of −<90 kd and an effective amount of an antigen concurrently.

This invention also provides a method of producing a T-independent conjugate comprising conjugating a microbial antigen or an epitope thereof to α(1,6) dextran.

As used herein microbial antigen proteins or epitopes thereof include bacterial and viral proteins, carbohydrate molecules, and epitopes thereof. Microbial antigens include but are not limited to Cytomegalovirus, Mycobacterium avium, and Cryptoccocus. One of ordinary skill in the art will be readily familiar with numerous additional bacteria and viruses whose proteins, polysaccharides, and epitopes thereof may be used in the above-described methods.

In another embodiment of the above-described methods, the microbes are Cytomegalovirus, *Mycobacterium avium*, or Cryptoccocus.

In a further embodiment of the method, the microbial protein antigen or an epitope thereof is conjugated to α(1,6) dextran by a heteroligation technique.

This invention also provides a method of inducing antigen specific IgA in a subject, wherein the antigen is a microbial protein, carbohydrate or a fragment thereof comprising administering a therapeutically effective amount of the T-independent conjugate vaccine produced by a method of producing a T-independent conjugate comprising conjugating a microbial antigen or an epitope thereof to α(1,6) dextran to the subject.

This invention also provides a method of inducing antigen specific IgA in a subject, wherein the antigen is a microbial antigen or epitope thereof comprising administering α(1,6) dextran and an effective amount of an antigen sequentially or concurrently.

In an embodiment of either of the above-described methods the subject is T-cell deficient.

In the embodiment of method of either of the above-described methods of inducing antigen specific IgA the subject is not T-cell deficient.

This invention further provides a method of treating a microbial infection in a subject comprising the method inducing antigen specific IgA in a subject, wherein the antigen is a bacterial envelope protein or a fragment thereof comprising administering a therapeutically effective amount of the T-independent conjugate vaccine produced by a method of producing a T-independent conjugate comprising conjugating a microbial antigen protein or an epitope thereof to α(1,6) dextran to the subject.

In an embodiment of method of any of the above described methods of inducing antigen specific IgA in a subject, the microbial infection is an opportunistic infection. Examples of opportunistic infections include but are not limited to infections by Cytomegalovirus, *Mycobacterium avium*, or Cryptoccocus.

In a further embodiment of the above described method, the subject is infected with HIV-1 or has AIDS.

This invention also provides a method of treating a microbial infection in a subject comprising the method of inducing antigen specific IgA in a subject, wherein the antigen is a microbial antigen or epitope thereof comprising administering α(1,6)dextran and an effective amount of an antigen sequentially or concurrently.

This invention further provides a method of preventing a microbial infection in a subject comprising the method of inducing antigen specific IgA in a subject, wherein the antigen is a bacterial envelope protein or a fragment thereof comprising administering a therapeutically effective amount of the T-independent conjugate vaccine produced by a method of producing a T-independent conjugate comprising conjugating a microbial antigen protein or an epitope thereof to α(1,6) dextran to the subject.

This invention further provides a method of preventing a microbial infection in a subject comprising the method of inducing antigen specific IgA in a subject, wherein the antigen is a microbial antigen or epitope thereof comprising administering α(1,6)dextran and an effective amount of an antigen sequentially or concurrently.

In an embodiment of method of the above-described methods of inducing antigen specific IgA in a subject, methods of treating a microbial infection in a subject comprising the method of inducing antigen specific IgA in a subject; and methods of preventing a microbial infection in a subject comprising the method of inducing antigen specific IgA in a subject 58, the T-independent α(1,6)dextran conjugate is administered to a mucosal surface of the microbial infected subject or via a systemic route of vaccination.

In an embodiment of method of the above-described methods of inducing antigen specific IgA in a subject, methods of treating a microbial infection in a subject comprising the method of inducing antigen specific IgA in a subject; and methods of preventing a microbial infection in a subject comprising the method of inducing antigen specific IgA in a subject the administration is topical, oral, nasal, anal, liposome-mediated delivery, aerosol delivery, intravenous delivery or subcutaneous delivery.

This invention also provides a composition comprising a T-independent conjugate in an amount effective to induce antigen specific IgA in a subject and a pharmaceutically acceptable carrier.

This invention also provides a method of producing a composition comprising a T-independent conjugate in an amount effective to induce antigen specific IgA in a subject and a pharmaceutically acceptable carrier comprising the method of claim 1 and further comprising admixing the T-independent conjugate and the pharmaceutically acceptable carrier.

This invention provides a composition comprising an effective amount of a T-independent conjugate and a pharmaceutically acceptable carrier, wherein the T-independent conjugate is produced by the method of claim 1.

This invention provides a composition comprising a effective amount of a T-independent conjugate and a pharmaceutically acceptable carrier, wherein the T-independent conjugate is produced by the method of producing a T-independent conjugate comprising conjugating a microbial antigen or an epitope thereof to α(1,6) dextran.

This invention also provides the use of the α(1,6) dextran molecule identified as a potent antibody activator in claim 1 as a carrier or an adjuvant for vaccines to enhance mucosal immunity.

This invention provides a method of identifying an α(1,6) dextran molecule as a potent IgA-B cell activator, wherein the T-independent conjugate is used as a vaccine to induce antigen specific IgA.

1) The Concept of the T-independent Conjugate-vaccines.

The T-independent property of microbial polysaccharides has been well-documented[22] and was briefly described in the background section. The successful application of the "T-dependent conjugate-vaccines" for more than a decade has strongly influenced the direction of the field of vaccine development in such a way that certain advantages of the T-independent antigen and their potential applications have been almost completely ignored. These include application in the field of HIV vaccination. Our finding that a classical TI-II antigen, α(1,6)dextran can elicit a strikingly enhanced IgA response in the absence of T-cells (FIG. 1) led to the thoughts of an alternative direction, i.e., the development of the "T-independent conjugate-vaccines".

By definition, the T-independent conjugate-vaccines are newly generated molecules produced by coupling an antigenic determinant or an antigenic molecule to a T-independent carrier molecule, such as a polysaccharide. Such conjugates retain the given antigenic specificities and also the property of the carrier molecule itself. They may be completely T-independent, such as a hapten-polysaccharide conjugate; or could be "semi-T-independent' as when a protein molecule is coupled to a polysaccharide. The latter may function like a T-independent antigen in the initial stimulation of immune cells but show the T-dependent reactivities after the protein is processed in vivo.

Our goal is to use the potential advantages of TI-antigens for the development of a vaccination strategy. These include their ability to work well in the absence of functional T-cells; and the unique properties of a particular carbohydrate molecule, which may determine its in vivo processing by host cells, cellular compartment localization and its interacting lymphocytes (see Ref. (22), for a recent review). The structural diversity of carbohydrate molecules, the polymorphism of microbial polysaccharides and of animal cell derived carbohydrate-containing molecules and the development of the synthetic polymer industry provide an un-limited resource for the application of our concept of the "T-independent conjugate-vaccines".

2) Identification of α(1,6)dextran as a Carrier Molecule for Producing the "T-independent Conjugate-vaccines" and as an Adjuvant for IgA Induction.

Antibody of IgA isotype plays important roles in mucosal immune response to foreign antigen. Induction of specific IgA to HIV proteins may eradicate the invaded virus on the mucosal surface at the local sites before the systemic infection occurs. Vaccines directed to IgA production are thus critical in preventing HIV infection. We identify here α(1, 6)dextran as a suitable carrier for the production of a class of T-independent conjugate-vaccines designed to elicit the antigen specific IgA response. In addition, α(1,6)dextran itself can serve as an adjuvant for enhancing IgA response.

Figure 4:
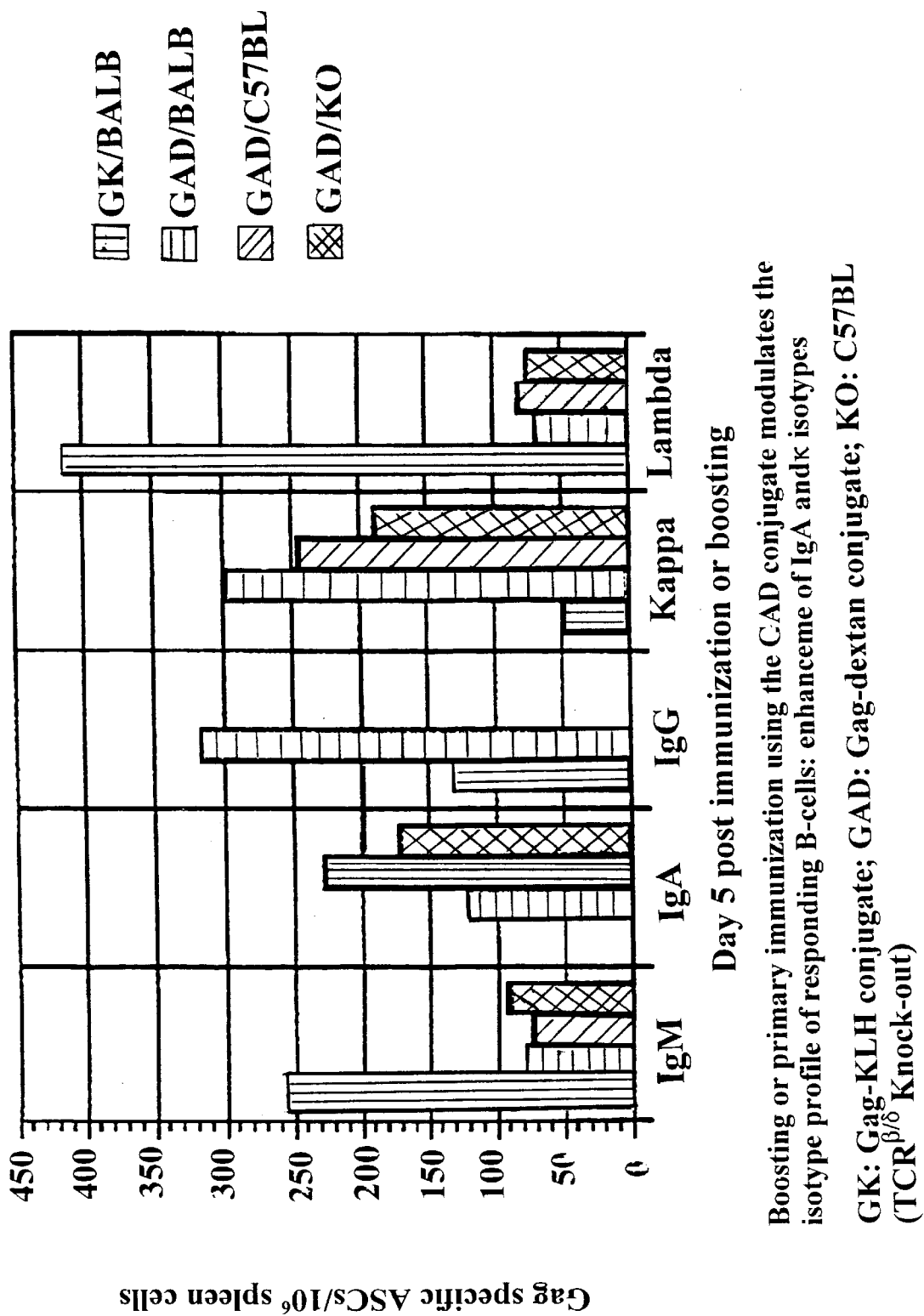
FIG. 4: Boosting or primary immunization using the GAD conjugate modulate the isotype profile of responding B-cells: enhancement of IgA and K L-chain isotype. GK: Gag-KLH conjugate; GAD: Gag-dextran conjugate; KO: C57BL(TCRβ/δ Knock-out) This figure summarized two separate experiments applying GAD conjugate, which is composed of the Gag protein of HIV-1 and α(1,6)dextran. Different immunization strategies were applied. In the groups of GK/BALB and GAD/BALB, Balb/c mice were immunized by i.v. injection of purified 100 μg of Gag-GST fusion protein mixed with FCA, two weeks late, injected (i.p.) with 50 μg of Gag-KLH conjugate mixed with IFA; at the fourth week, the GK/BALB group were boosted with 12.5 μg of Gag-KLH and the GAD/BALB group with 10 mg GAD conjugate by i.v. injection. The remaining two groups were immunized by only one i.v. injection of 10 μg GAD conjugate. At the 5th day after the last boosting or the primary immunization, the antigen-specific ELISAspot assays were performed to detect the number of ASC specific for the Gag protein and for the carrier, α(1,6)dextran.

Native dextran N279 is a near-linear macromolecule of glucose with 90% α(1→6), 5% α(1→)[1] and 5% α(1→3) linkages,(24) derived from *Leuconostoc mesenteroides*, strain NRRL B512. The predominant α(1→6) glycosidic linkages make it uniquely flexible. Differing from other glycosidic bonds, three torsion (rotational) angles, φ, ψ and ω are required to define the conformation of an α(1→6) linkage. It is also very stable in vivo, since no mammalian enzyme can digest the linkage. After injection, the polysaccharide was found to be trapped and persist in the splenic folicles, leading to the formation of antigen specific germinal centers(25). In humans, a (1→6)dextran of relatively smaller molecular weight has been safely applied as blood expander for many years(26). Most importantly, we showed in this report that α(1,6)dextran can elicit a markedly enhanced IgA response in T-cell free mice (FIG. 1); co-injection of the molecule with other antigens can enhance the IgA response to the co-antigen (FIG. 2); and a dextran-Gag conjugate can elicit the Gag-specific IgA (FIG. 4).

[1] This symbol designates the attachment of a terminal nonreducing end ugar to an adjacent residue by α(1→6)linkage and other glucopyranosidic onds[24]

Figure 2:
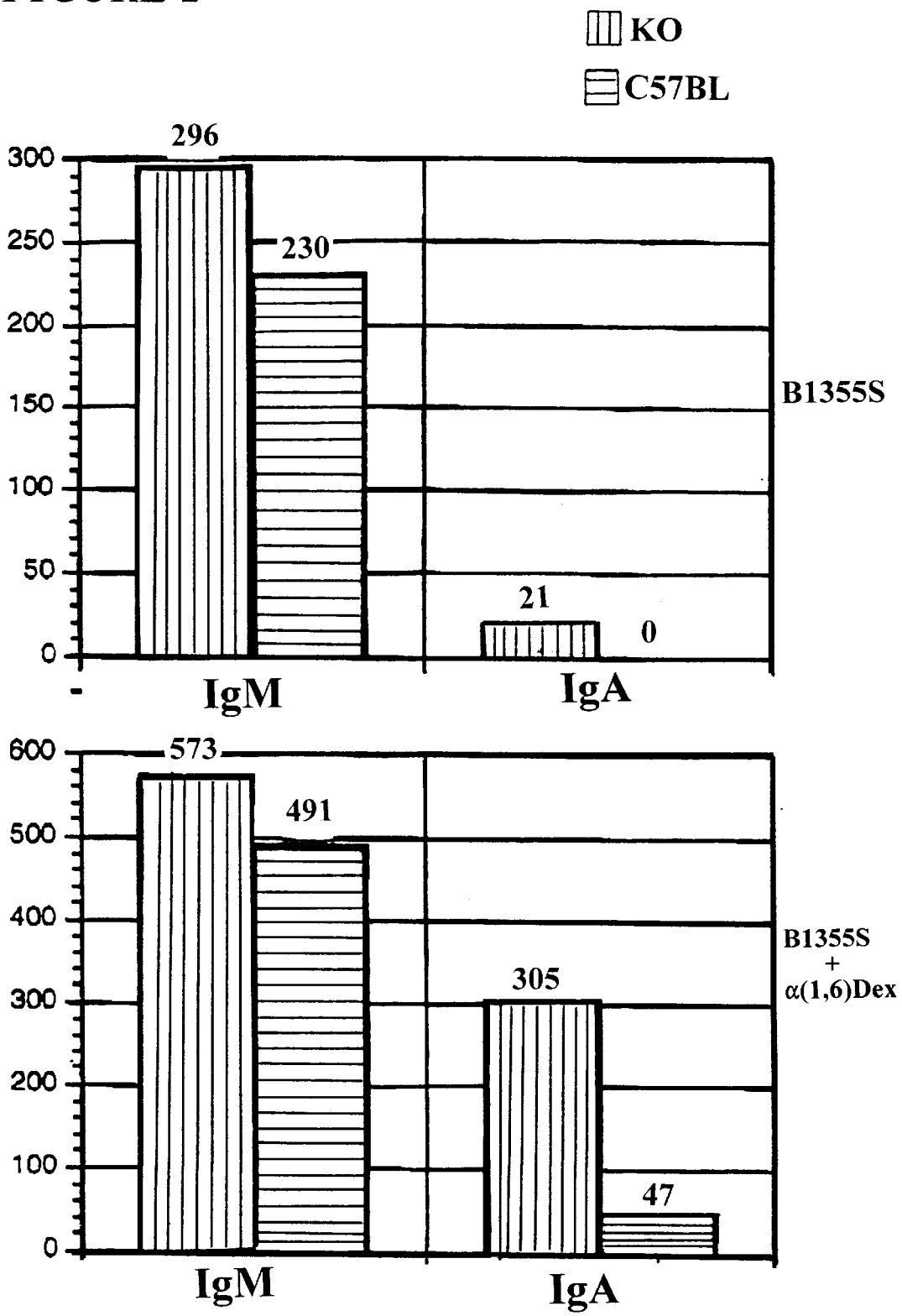
FIG. 2: Co-stimulation with α(1,6)dextran, the B1355S-specific IgA response was extensively enhanced in the KO mice. The KO mice and C57BL normal controls were immunized by i.v. injection of 10 μg polysaccharide B1355S each mouse or with 10 μg each of B1355S and α(1,6)dextran (Mix-Ags). At day 5 post-immunization, antigen-specific ELISAspot assay were performed as described above (Legend for FIG. 1). In contrast to α(1,6)dextran, B1355S alone is not able to elicit IgA response in both KO and normal C57BL mice. Co-injection with α(1,6)dextran, however, led to the induction of significant amount of IgA-ASCs specific for B1355S in KO mice and to much less extent in C57BL. In the same experiment, we applied α(1→3)α(1→6)dextran (B1355S). By contrast, this polysaccharide (B1355S) was not able to elicit antigen specific IgA in both KO and normal C57BL mice (FIG. 2 Top portion). Thus, α(1→6)dextran, but not α(1→3)α (1→6)dextran, can induce T-independent IgA responses, emphasizing the importance of the structural properties of stimulating antigen in the induction of IgA. As described above, the two polysaccharides differ only in their glycosidic linkage composition, providing us with important clues for identifying the structural characteristics critical for IgA induction (Aim 1).
Figure 3:
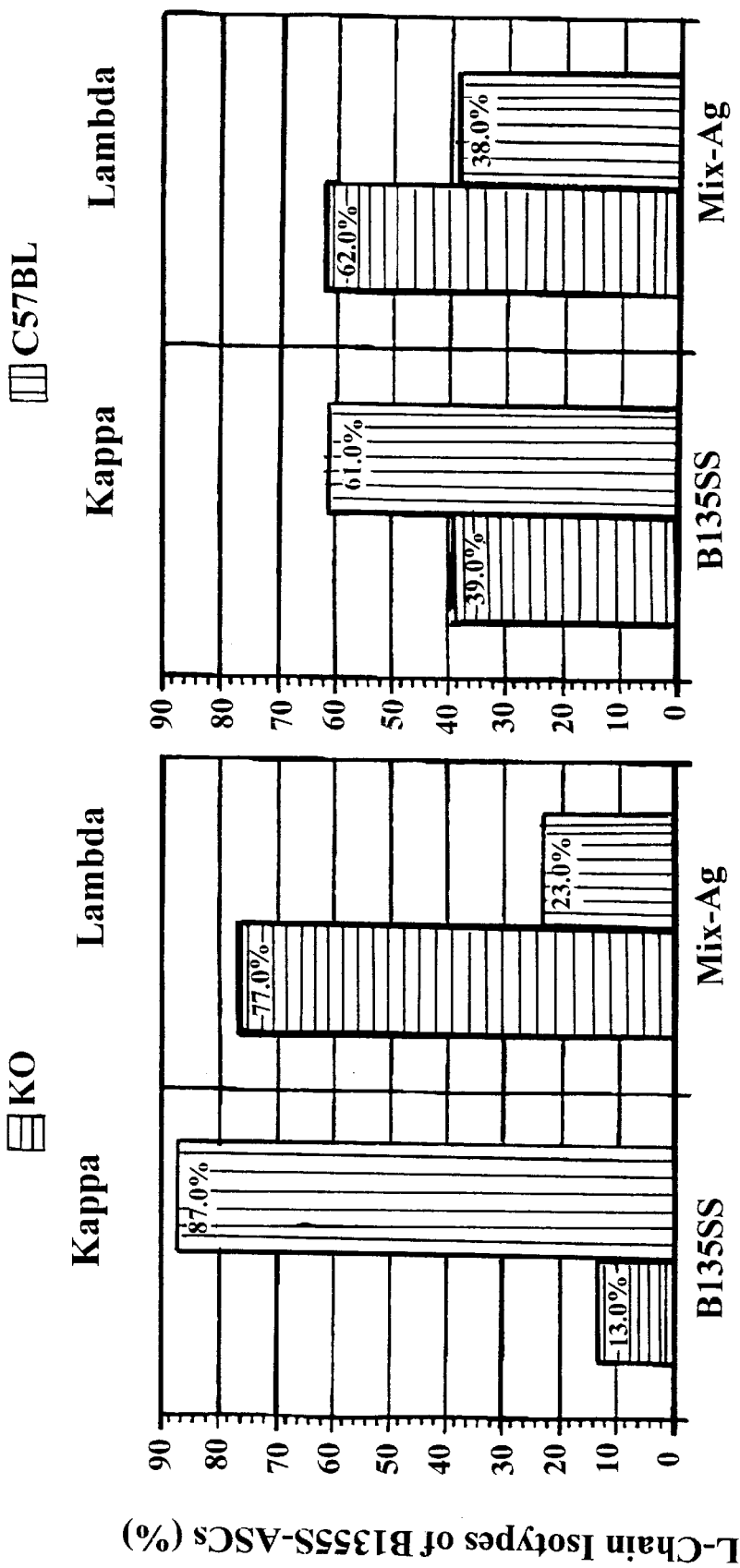
FIG. 3: Co-immunization with α(1,6)dextran, the B1355S-specific B-cell response switched to K light Chain predominant, resulting in an extended repertoire of responding B-cells in both T-cell free mice (KO, C57BL,TCRβ/δ) and normal mice(C57BL). In response to the B1355S stimulation, both KO and normal mice produced dominantly antibodies of λ L-chain; this profile was however inverted to K light Chain predominant, by the co-stimulator, α(1,6) dextran. Our previous studies showed that antibodies to α(1,6)dextran have no or very limited cross-reactivity to B1355S. The two microbial polysaccharides are structurally distinct, see ref.[22] for a review. Thus, these data demonstrated that α(1,6)dextran can modulate the isotype profile and the repertoire of the responding B-cell to a given antigen.

Data illustrated in FIGS. 2 & 3 indicated an additional application of α(1→6)dextran, i.e., to apply it directly on a mucosal surface wherein an infection occurred and a specific antibody response were taking place. Introducing this non-toxic molecule locally may help to reshape the repertoire of responding cells and their H & L chain isotypes.

3) A Combinatorial Vaccination Strategy Applying Both TI- and TD Conjugates.

As illustrated in FIG. 4, an immunization directed to the Gag polyprotein of HIV-1 was initiated by a T-dependent antigen and finally boosted using a semi-TI conjugate-vaccine, the GAD conjugate. The GK-group of mice, who were immunized by Gag-GST and boosted with Gag-KLH, specific IgG but not IgA was induced. Boosting with the GAD conjugate elicited both IgG and IgA. In addition, the repertoire of the responding B-cells switched to kappa light chain predominance. These data demonstrated a vaccine strategy that combines the advantages of both TD and TI conjugate-vaccines.

In most AIDS patients, the antibody response to HIV protein was already initiated by the infection. Vaccination with the TI-conjugates alone may be sufficient to induce a protective response having antibodies of both IgG and IgA isotypes. Boosting with TI-conjugates can be an important addition to all current HIV vaccination strategy. A TI-conjugate composed of α(1→6)dextran and the Env protein of HIV-1 or its functional epitopes shall be developed to meet the current needs.

4) Methodology in Producing the T-independent Conjugate-vaccines

A) The GAD type of conjugates: The GAD stands for Gag, Avidin and α(1,6)Dextran. The dextran molecule was coupled with Biotin-LC-Hydrazide (PIERCE, 21340X) and then linked to a biotinylated protein by avidin. The use of Biotin-LC-Hydrazide introduces an extended spacer arm between the molecules.

a. Oxidization of dextran to produce CHO groups. α(1,6) dextran, preparation N279 (B512), was dissolved in 0.01M $N_a$Acetate buffer, pH5.5, at 10 mg/ml and warmed in 37° C. water bath for 30 minutes. $N_aIO_4$ was then added to the final concentration of $1\times10^{-2}$ M. Mix the solution well and let it stand at room temperature for one hour in dark. Dialyze the preparation against 0.02M BBS(Borate buffered saline) pH8., 4° C., overnight;

b. Coupling of Biotin-LC-Hydrazide to the oxidized dextran. The above oxidized dextran was diluted 10 fold in 0.1 M $N_a$Acetate pH5.5. A 1/3 volume of 5 mM Biotin-LC-Hydrazide was added drop wise. The mixture was shaking at RT for one hour. The reaction was terminated by addition of 0.5 ml of 1 M Tris HCL, pH7.5. The mixture was then dialyzed against Tris buffer (0.1M Tris pH7.5, 0.1M NaCl, 2.0 mM MgCl2);

c. Coupling of NHS-Biotin(BRL #5533LA) to Gag. Standard method was applied for the coupling reaction. The Gag protein of HIV-1 was expressed as Gag-GST fusion protein in E. coli. and purified by Glutathione-agarose beads(Sigma, G4510) by the manufacture's standard protocol.

d. Link the two biotinylated molecules by avidin. The biotinylated Gag, avidin and the biotinylated dextran were mixed at the molar ratio of 20:4:1 and nutating at RT for two hours. The conjugate was kept at 4° C. before application.

B) Glutaraldehyde-conjugation

Amino-dextrans(Molecular Probes, D-7144, D-1861, D-7145) were coupled to Gag protein by Glutaraldehyde. Glutaraldehyde was added to the mixtures of Gag and amino-dextran to the final concentration of 0.2%. They were nutating at RT for two hours. The reaction was stopped by addition of 1 M Ethanolamine at 6.1 ml/ml. The mixture was nutated at RT for additional 2 hours and then dialyzed against 1×PBS, overnight.

C) An ELISA-based Method for Monitoring the Quality of a Conjugate a. Coat ELISA plate with monoclonal anti-dextran, 45.21.1 (α,λ), at 5 μg/ml, in 0.1 M $N_a$HCO$_3$ pH9.6, 37° C., 2 hours; Wash the plates using ELISA washing solution in(1×PBS, 0.05% Tween20, 0.025% NaAzide) and blocked with the same solution containing 1% BSA;

b. Incubate the coated plates with serial dilution of the conjugate at 37° C. for 2 hours then wash them with ELISA washing solution;

c. Incubate with antibodies specific for different epitopes of a given protein at 37° C. for 2 hours then wash them with ELISA washing solution;

d. Incubate with a second antibody specific for the isotype of the anti-protein antibody used above to monitor the conjugated epitopes; in separate wells, apply an alkali phosphatase(AP)-labeled anti-dextran, such as 45.21.1-AP, to detect the available epitopes of the carrier.

Our experience indicates that this method is valuable for monitor the quality of the TI-conjugates. Results correlate well with in vivo induction of the antibody response by a conjugate.

REFERENCES FOR THE FIRST SERIES OF EXPERIMENTS

1. Dochez, A. R. & Avery, O. T. *J. Exp. Med.* 26, 477–493 (1917).
2. Heidelberger, M. & Avery, O. T. *J. Exp. Med.* 38, 73–80 (1923).
3. Basten, A. & Howard, J. G. in *Contemporary Topics in Immunobiology* (ed. Davies, A. J. S.) 265 (Plenum, N.Y., 1973).
4. Humphrey, J. H., Parrott, D. M. V. East, *J. Immunology* 7, 419–439 (1964).
5. Weissman, I. L., Gutman, G. A., Friedberg, S. H. & Jerabek, L. *Adv. Exp. Med. Biol.* 66, 229–237 (1976).
6. Scher, I. *Adv. Immnunol.* 33, 1–71 (1982).
7. Berek, C. & Ziegner, M. *Immunol. Today.* 14, 400–404 (1993).
8. Kroese, F. G. M., Timens, W. & Nieuwenhuis, P. *Curr. Topics Path.* 84, 103–148 (1990).
9. Kraal, G., Weissman, I. L. & Butcher, E. C. *Nature* 298, 377–379 (1982).
10. Howard, J. in *Towards Better Carbohydrate Vaccines. Proceedings of a meeting organized by the World Health Organization*, Oct. 9–11, 1986, Geneva (eds. Bell, R. & Torrigiani, G.) 221–229 (John Wiley & Sons, Chichester New York Brisbane Toronto Singapore, 1987).
11. Robbins, J. B. & Schneerson, R. *J. Infct. Dis.* 161, 821–832 (1990).
12. Schneerson, R., Barrera, O., Sutton, A. & Robbins, J. B. *J. Exp. Med.* 152, 361→376 (1980).
13. Madore, D. V., et al. *Pediatrics* 85, 331→337 (1990).
14. Ahonkhai, V. I., et al. *Pediatrics* 85, 676–681 (1990).
15. Schneerson, R., Robbins, J. B., Szu, S. C. & Yang, Y. in *Towards better carbohydrate vaccines Proceedings of a meeting organized by the World Health Organization*, Oct. 9–11, 1986, Geneva (eds. Bell, R. & Torrigiani, G.) 307–327 (John Wiley & Sons, Chichester New York Brisbane Toronto Singapore, 1987).
16. Varmus, H. E. in *Mobile Genetic Elements* (ed. Shapiro, J. A.) 411–501 (Academic Press, New York, 1983).
17. Sabin, A. B. *Proc. Natl. Acad. Sci. USA* 89, 8852–8855 (1992).
18. Kohler, H., Goudsmit, J. & Nara, P. *J. Acq. Imm. Def. Synd.* 5, 1158–1168 (1992).
19. Nara, P. L., Garrity, R. R. & Goudsmit, J. *FASEB J.* 5, 2437–2455 (1991).
20. Wang, D., Stall, A. M. & Kabat, E. A. in *The 9th International Congress of immunology* (ed. AAI) 515 (San Francisco, Calif., 1995).
21. Wang, D., et al. in *7th International Workshop of WACIID* (Ikoino Mura, Yamagata, Japan., 1995).
22. Wang, D. & Kabat, E. A. in *Structure of Antigens* (ed. Regenmortal, M. H. V. V.) 247–276 (CRC Press, Boca Raton New York London Tokyo, 1996., 1996).
23. BRIAND, J., et al. *Proc. Natl. Acad. Sci. USA* In press (1997).
24. Jeanes, A. *Mol. Immunol.* 23, 999–1028 (1986).
25. Wang, D., Wells, S. M., Stall, A. M. & Kabat, E. A. *Proc. Natl. Acad. Sci. USA* 91, 2504–2506 (1994).
26. Kabat, E. A. & Berg, D. *J.Immunol.* 70, 514–532 (1953).

Second Series of Experiments

Antibodies of the IgA isotype are believed to be the major mediator of the B cell-derived immunity at mucosal sites.

Induction of antigen-specific IgA in rectal and genital mucosa can be particularly important in protection against sexually transmitted pathogens, such as the human immunodeficiency virus (HIV-1). For years, investigations have focused primarily on the T-dependent route of B-cell activation that leads to induction of antigen specific IgA. In contrast, little effort has been performed to explore the T-independent route of IgA induction. It has been known for decades that some thymus-independent antigens can induce IgA responses. Recent establishment of a strain of T-cell deficient mice (C57BL, $\alpha\beta/\gamma\delta$ T-cell receptor knock-out, -/- mice) provided us a simplified model to investigate the T-independent B-cell responses in vivo in the absence of any T-cell. When a specific microbial polysaccharide, $\alpha(1\rightarrow6)$ dextran, was injected into these mice, a large number of antigen-specific B-cells, predominately of the IgA isotype, were elicited. The number of antigen specific IgA-secreting cells in spleen was about 30 fold higher than those in normal mice or mice injected with a structurally distinct polysaccharide, B1355S. These findings illustrated clearly the presence of a T-independent (TI) route of IgA induction in living animals and identified a polysaccharide antigen, $\alpha(1\rightarrow6)$dextran, as a potent stimulator of IgA-secreting B cells. In this proposal, we plan to investigate: 1) Can $\alpha(1\rightarrow6)$dextran serve as a carrier and/or adjuvant to elicit IgA responses to other antigenic determinants? 2) Can $\alpha(1\rightarrow6)$dextran-containing conjugates facilitate IgA responses to the gp120 glycoprotein of HIV-1? 3) What are the optimal route(s) of administration of these antigens to elicit antigen specific IgA at mucosal sites? With the unique T-independent characteristics, this category of vaccines can be effective not only in normal individuals but also in AIDS patients whose T-cell systems are severely impaired, serving as therapeutic vaccinations against HIV. The principle may also be applied to develop vaccines against opportunistic infections that occur frequently in AIDS patients and in other T-cell deficient syndromes.

1. Specific Aims

Our long-term goal is to understand mechanisms of host recognition and antibody responses to microbial antigens and to develop vaccines against infectious diseases. In this study, we take advantage of a simplified model system, the immune response of T cell deficient mice to microbial polysaccharide $\alpha(1\rightarrow6)$dextran, to study the T-independent routes of B-cell activation that leads to induction of antigen specific IgA and to explore it for the development of an alternative vaccination strategy against HIV-1. Our specific aims are:

Aim 1. To determine whether $\alpha(1\rightarrow6)$dextran can serve as a carrier and/or an adjuvant to elicit IgA responses to other antigenic determinants.

Aim 2. To develop a novel category of TI-conjugates applying $\alpha(1\rightarrow6)$dextrans to facilitate IgA responses to the gp120 glycoprotein of HIV-1.

Aim 3. To investigate the optimal route(s) of administration of these TI-conjugates to elicit antigen specific IgA at mucosal sites.

Aim 4. To characterize the specificities and HIV-1 neutralization efficiency of IgA antibodies elicited by the T-independent route of immunization.

2. Background and Significance

Mucosal surfaces are protected against infectious microorganisms by the mucosal immune system, of which secretory IgA (s-IgA) is the major humoral defending factor (1, 2). s-IgA is polymeric and is structurally suitable for trapping and clearance of microorganisms in mucosal secretions. A receptor-mediated mechanism effectively transports s-IgA across epithelium to secretions. In the human, the amount of s-IgA exported onto mucosal surfaces can be more than 3 gm per day, far exceeding the amounts of IgG produced for circulation (1, 3, 4). They are frequently reactive with microorganisms in the local mucosal microenvironment, regulating the equilibrium between the host and their resident microorganisms (5, 6). The presence in mucosal secretions of s-IgA specific for microbial antigens highlights the feasibility of developing vaccines directed toward enhancement of mucosal IgA responses.

Natural infection by HIV-1, however, does not elicit a protective IgA response to HIV-1. Many factors may be responsible. These include the intracellular transmission characteristics of the retrovirus (7, 8), masking of the neutralization epitopes of the envelope glycoprotein (gp120) by glycosylation or by other structural elements (9–11), rapid turn-over dynamics of viral replication (12, 13) and the high mutation rates of their RNA genome (12, 14, 15). In addition to these intrinsic properties of the retrovirus, the immune deficiency they induced in AIDS patients further hampers the host responses to the virus. Owing to the specific mechanisms of viral entry, i.e., the specific molecular interactions of gp120 with CD4 and chemokine receptors, T-cell depletion takes place selectively and continuously in AIDS patients. Their cellular and humoral immunity, including the mucosal IgA responses to HIV-1 and other pathogens, are seriously impaired. As a consequence of the T-deficient characteristics of the disease, opportunistic infections typically cause death in humans with the disease. Thus, a paradox is created by the retroviral infection: effective vaccinations require functions of T-cells which, however, are irreversibly destroyed by the viral infection.

Are there alternative routes of IgA induction under T cell compromised conditions? It has been known for some time that some thymus-independent antigens (16), such as microbial polysaccharide $\alpha(1\rightarrow6)$ dextran, can induce antigen specific IgM and IgA antibodies in normal and nude (-/-) mice (17–19). Recognition of a T-cell independent route of IgA induction in vivo was only established recently with studies on the gene-knock out mice that are free of T-cells. This strain was produced by knocking-out both $\gamma\delta$ and $\alpha\beta$ T cell receptors(TCR) (20). Unlike nude (-/-) mice, whose thymus-independent, gut-associated T cell system remains intact (21, 22), these KO mice are completely free of T cells (20). Interestingly, immunohistology revealed the presence of IgA producing B cells in the gut and found no germinal center in their lymphoid tissues (20). Thus, in the absence of functional T cells and germinal center, class switching of IgM to IgA took place in these KO mice. When they were challenged with Rotavirus, a reduced yet significant number of IgA-secreting B cells were elicited in the gut, contributing significantly to an effective protection from the gastroenteric pathogen (23). These IgAs were found to be directed exclusively to a viral structural protein, VP6, that forms a repetitive structure in the rotaviral particle. IgA specific for another viral surface protein, VP4, was not detected in KO mice, although IgA specific for both VP6- and VP4 were seen in normal C57BL/6 mice. Thus, although T-cells play important roles in the mucosal IgA responses to protein antigens, they are not necessary for the induction of IgA specific for VP6 protein, indicating the involvement of an alternative route of IgA induction that is completely independent of T lymphocytes and their specific cytokines. The importance of structural characteristics of stimulating antigens in IgA induction is implicated by these studies.

The notion of T-independent routes of IgA induction was further established by our recent investigations of B cell responses to microbial polysaccharides in T cell-deficient mice. The strain of KO mice($\gamma\delta/\alpha\beta$ TCR, -/-) in a C57BL background has recently become available from Jackson Laboratories. When native $\alpha(1\rightarrow6)$dextran N279 was injected into these mice, a large number of $\alpha(1\rightarrow6)$dextran-specific B-cells, predominately of the IgA isotype, were elicited. The number of antigen specific IgA-secreting cells in the spleen was about 30 fold higher than those in C57BL/6J mice immunized by the same antigen. The levels of anti-$\alpha(1\rightarrow6)$dextran IgA in serum and in gut mucosal secretions were also markedly elevated in the KO mice as compared with normal C57BL immunized with the same antigen. To see if induction of IgA in the absence of T cells is a common characteristics of TI-antigens, we introduced an additional TI-antigen, $\alpha(1\rightarrow3)\alpha(1\rightarrow6)$dextran (B1355S) in our studies. Unlike $\alpha(1\rightarrow6)$dextran, this TI-antigen was unable to elicit antigen-specific IgA in either the T cell-free mice or normal C57BL controls. Thus, some but not all microbial polysaccharides can induce the T-independent route of IgA induction: $\alpha(1\rightarrow6)$dextran but not $\alpha(1\rightarrow3)\alpha(1\rightarrow6)$dextran (B1355S) is identified as a potent stimulator of IgA-response. The pathway of B cell activation and differentiation triggered by $\alpha(1\rightarrow6)$dextran is completely T-cell independent.

The structure of $\alpha(1\rightarrow6)$dextran has been well characterized. Native dextran N279 is a near-linear macromolecule of glucose with 90% $\alpha(1\rightarrow6)$, 5% $\alpha(1\rightarrow)$ and 5% $\alpha(1\rightarrow3)$ linkages (24) derived from Leuconostoc mesenteroides, strain NRRL B512. The predominant $\alpha(1\rightarrow6)$ glycosidic linkages make it uniquely flexible. Differing from other glycosidic bonds, three torsion(rotational) angles, $\phi, \gamma$ and $\omega$ are required to define the conformation of an $\alpha(1\rightarrow6)$linkage (17). It is also very stable in vivo, since no mammalian enzyme can digest the linkage. After injection, the polysaccharide was found to be trapped and persist in the splenic follicles, leading to the formation of antigen specific germinal centers (18). $\alpha(1\rightarrow6)$dextran is recently identified as a natural ligand of the mannose receptor, which is expressed by follicular dendritic cells and some macrophages (25), providing a possible explanation of selective tissue localization of the polysaccharide. In humans, $\alpha(1\rightarrow6)$dextran of relatively smaller molecular weight has been safely applied as blood expander for many years (26). $\alpha(1\rightarrow6)$ dextran can also be used during surgery as a prophylactic agent to prevent deep venous thrombosis, since the mannose receptor-mediated clearance of tissue-type plasminogen activator (t-PA) can be inhibited by $\alpha(1\rightarrow6)$dextran (27). Thus, there is little safety concern if $\alpha(1\rightarrow6)$dextran is used for human vaccination.

In summary, accumulating evidence indicates the presence in vivo of a T-independent route of IgA induction in addition to the conventional T-dependent pathway of IgA responses. Our recent studies of B cell responses to microbial polysaccharides in T cell deficient mice identified a specific microbial polysaccharide, $\alpha(1\rightarrow6)$dextran (N279), as a potent IgA activator. It acts in the presence and absence of functional T cells. We hypothesize: 1) An intrinsic structural property of $\alpha(1\rightarrow6)$dextran, the most flexible $\alpha(1\rightarrow6)$ glycosidic linkage that renders it superior in presenting multiple antigenic determinants for B cell cross-linking activation, is necessary but not sufficient for IgA induction. 2) Its selective cellular and tissue localization, mediated by mannose receptor and/or via other mechanisms, may lead to induction of an unique cytokine profile, contributing significantly to the microenvironment necessary for the activation of B cell-class switch to IgA. We propose, therefore, that $\alpha(1\rightarrow6)$dextran of proper molecular weight can serve as a carrier to present other antigenic determinants, such as those derived from the envelope protein(gp120) of HIV-1, to induce IgA responses against HIV-1. Preliminary studies supporting this proposal are summarized in the next section.

3. Progress Report

As described below and in a recent review article (17), this study extends in a new direction of previous research on the structure and specificity of antibody combining-sites.

Direct Evidence Demonstrating the Existence of T-independent Routes of IgA Induction As described above, studies using nude(-/-) mice did not completely clarify whether the T-cell plays any role in the TI-responses. A strain of genetically manipulated T cell-free mice was thus introduced. By crossing TCR-$\beta$ mutant mice with TCR-$\delta$ mutant mice, TCR-bXd double mutant mice were generated, resulting in the first strain of T-cell-free mice in a mixed (129X C57BL/6) background (20). This strain was back-crossed further to C57BL/6, forming almost a congenic strain of T cell-free mice of C57BL/6 (Peter Mombaerts, personal communication).

These mice and normal controls were immunized with two classical T-independent polysaccharides, $\alpha(1\rightarrow6)$ dextran (N279) and $\alpha(1\rightarrow3)\alpha(1\rightarrow6)$ dextran (B1355S). As shown in FIG. 1, a large number of $\alpha(1\rightarrow6)$dextran-specific B-cells, predominately of the IgA isotype, were elicited in the KO mice. The number of antigen specific IgA-secreting cells in the spleen is about 30 fold higher than those in C57BL/6J mice. These findings illustrated clearly the presence of a T-independent (TI) route of IgA induction in living animal, providing a simplified model to investigate the underlying cellular and molecular mechanisms(Aim 1).

Structural Properties of the Stimulating Antigen are Critical for Induction of IgA As shown in FIG. 2. top portion, a structurally distinct polysaccharide, $\alpha(1\rightarrow3)\alpha(1\rightarrow6)$dextran, B1355S, did not elicit an IgA response in either KO or normal C57BL mice. There are at least two explanations for the distinct responses to the two dextrans: 1) The intrinsic reactivity of the responding B cells is the determining factor for their class switching. In fact, antibody responses of both Balb/c (28) and C57BL (29) to B1355S have been shown to be highly restricted in IgM isotype. In contrast, the two strains produce anti-$\alpha(1\rightarrow6)$dextrans of both IgM and IgA isotypes (17-19, 30); and 2) The microenvironment is responsible for the induction of IgA-B cells. It has been shown previously that the two dextrans have distinct pattern of cellular compartment localization (17). After administration, $\alpha(1\rightarrow6)$dextran was retained in splenic germinal centers and marginal zone in normal mice; $(1\rightarrow3)\alpha(1\rightarrow6)$dextran was only detectable in splenic marginal zones, but not in follicles. Thus, B cells meet and respond to the two dextrans in different microenvironments.

Co-stimulation with $\alpha(1\rightarrow6)$dextran, the B1355S-specific IgA Response was Extensively Enhanced in the KO Mice.

B cells of different lineage-origins, i.e., B-1 and conventional B cells, may have their unique properties (31, 32). B-cell responses to B1355S were found to be restricted to the B-1 cell population, as illustrated by Forster et al in Balb/c (33); whereas both B-1 and conventional B cells participated in the primary responses to $\alpha(1\rightarrow6)$dextran as demonstrated by our studies (34). If the lack of an IgA response to $\alpha(1\rightarrow3)\alpha(1\rightarrow6)$dextran is the intrinsic property of responding B cell, co-administration of $\alpha(1\rightarrow6)$dextran may not be able to change the isotype profile of anti-$\alpha(1\rightarrow3)$ $\alpha(1\rightarrow6)$dextran. The KO mice and C57BL normal controls were immunized by i.v. injection of 10 $\mu$g polysaccharide B1355S each mouse or with 10 $\mu$g each of B1355S and α(1→6)dextran (Mix-Ags). At day 5 post-immunization, antigen-specific ELISAspot assay were performed as described above (Legend for FIG. 1). In contrast to α(1→6) dextran, B1355S alone is not able to elicit IgA response in both KO and normal C57BL mice. Co-injection with α(1→6)dextran, however, led to the induction of significant amounts of IgA secreting cells specific for B1355S in KO mice and to much less extent in C57BL (FIG. 2 bottom). Thus, α(1→6)dextran, but not α(1→6)α(1→6)dextran, may activate certain cells in spleen in the absence of T-cells and lead to establishment of a cytokine profile which are necessary for B-cell class switching to IgA.

Taken together, these results are consistent with previous observation applying the T-cell KO mice of mix background (129XC57BL/6J). The presence of a T-independent route of IgA induction in living animal was clearly demonstrated, providing a simple model to investigate the underlying mechanisms. The co-immunization experiments (FIG. 2) illustrated further that as a potent IgA activator, α(1→6) dextran can enhance the IgA response to a structurally distinct microbial antigen (FIG. 2) and influence its antibody light chain repertoire (FIG. 3). The application potential of α(1→6)dextran in vaccine development is thus highlighted by these studies.

Research Design & Methods

These studies will focus on the following specific questions: 1) Can α(1→6)dextran serve as a carrier and/or adjuvant to elicit IgA responses to other antigenic determinants? 2) Can α(1→6)dextran-containing conjugates facilitate IgA responses to the gp120 glycoprotein of HIV-1? 3) What is the optimal route(s) of administration of these TI-conjugates for the induction of mucosal IgA? and 4) Can IgA antibodies elicited by these TI-conjugates neutralize a broad range of HIV-1 strains and what epitope-binding specificities can be responsible for the viral neutralization?

Aim 1: α(1→6)dextran as a Carrier and/or Adjuvant to Elicit IgA Responses

To trigger the onset of an immune response, a TI antigen must bind and cross-link several antigen receptors on the surface of the B-cells. The number of epitopes carried by a polymer is directly associated with its molecular weight (MW). The nature of the backbone structure of polysaccharides, including residues and glycosidic linkage composition, influence further their interaction with B cells (16, 17). How MW of α(1→6)dextran influences induction of IgA specific for a hapten carried by α(1→6)dextran is examined. Also investigated are the optimal conditions for the use of α(1→6)dextran as an adjuvant.

a) Optimal MWs of α(1→6)dextran-fluorescent(DEX-FITC) conjugates for induction of anti-fluorescent antibodies of IgA isotype To test whether α(1→6)dextran can serve as a carrier to present a small hapten for induction of IgA of a desired specificity and to identify the optimal MWs of the carrier for this purpose, α(1→6)dextran-fluorescent(DEX-FITC) conjugates are tested in both TCR-KO and C57BL mice. The DEX-FITC conjugates of different molecular weights, ranging from 4 KD to 2000 KD, are commercially available (Sigma). As reported by Fernandez and Moller (35), a preparation of DEX-FITC made from native α(1→6)dextran with a mixture of molecules of different M.W. is immunogenic in mice (35). Antibodies specific either for α(1→6) dextran or for FITC were elicited. The IgA responses to the conjugate was not investigated in the report. It is expected that the conjugates within certain M.W. ranges can be immunogenic in the TCR-KO mice. Thus, i.v. administration of DEX-FITC in these mice allows identification of the optimal M.W. of the carrier for the induction of anti-FITC responses.

Mice are immunized by i.v. injection of 10 μg of each antigen, 5–10 mice per group. The number of antigen specific antibody-secreting cells, including IgM, IgA, IgG, and Kappa or Lambda, will be determined at Day 5 by ELISAspot Assay as described (18). Briefly, 96-well microtiter plates are coated with α(1→6)dextran N279 at 10 μg/ml or with Ficoll-FITC. Bound antibodies are revealed with alkaline phosphatase-conjugated antibodies specific for murine antibodies of above different isotypes. Antibodies in serum and in gut secretions will be monitored by ELISA assays as described (36, 37). The optimal M.W. of the carrier for the induction of anti-FITC antibodies of the IgA isotype may differ from those for the anti-α(1→6)dextran specificity. This information is of importance to produce the TI-conjugates against HIV-1.

b) α(1→6)dextran as an IgA-adjuvant, its optimal MWs and concentration

As illustrated by the co-immunization experiments (FIG. 2), a mixed preparation of native α(1→6)dextran, N279, showed a strong "adjuvant" effect on the IgA response to a co-administrated polysaccharide, α(1→3)α(1→6)dextran. Investigated here are the optimal M.W. and concentration of α(1→6)dextran for its "adjuvant"-effect on the activation of IgA-B cells to the co-antigen, α(1→3)α(1→6)dextran. It is hypothesized that the adjuvant effect of α(1→6)dextran can be attributed to its ability to bind and stimulate some antigen presenting cells, such as dendritic cells and some macrophages expressing the mannose receptor. These events will lead to production of certain non-T cell cytokines, including TGF-β which is critical for IgA induction.

Given this hypothesis, it is predicted that the optimal M.W. of α(1→6)dextran for eliciting anti-dextran antibodies may differ from those required for its adjuvant effect. If the specific binding of α(1→6)dextran by the mannose receptor is critical for the adjuvant effect, the lower M.W. preparation of the molecule shall be sufficient. α(1→6)dextran with M.W. lower than 90 KD is not immunogenic (38) yet retain its specific binding by mannose receptor (25, 27). Since such preparations can be safely applied in the human in large dosage without side effect, the effective adjuvant with the lowest M.W. will be identified.

Aim 2. α(1→6)dextran as a Carrier Molecule for the Generation of the T-independent Conjugate-vaccines Against HIV-1

The optimal M.W. of α(1→6)dextran as identified above is used to produce the TI-conjugates for HIV-1 vaccination. A TI-conjugage may be "completely T-independent", such as the DEX-FITC conjugate; or could be "semi-T-independent" as when a protein or a peptide is coupled to the polysaccharide. The latter may function like a T-independent antigen in the initial stimulation of immune cells but show the T-dependent reactivities after the protein or peptide is processed in vivo. Two semi-TI conjugates, DEX-gp120 and Dex-LeY-peptide, will be prepared.

a) DEX-gp120 conjugates Many protein epitopes are conformational and composed of discontinuous amino acid residues. The DEX-gp120 conjugate is designed to present the gp120 in its native configuration and to take the advantage of α(1→6)dextran for IgA induction as well.

The DEX-gp120 conjugate is developed using a deglycosylated form of the wtΔ protein of gp120(10). The wtΔ protein of gp120 lacks the V1 and V2 variable loops but binds CD4 and CCR5 with high affinity. IgA antibodies specific for the regions interacting CD4 or CCR5 may specifically block HIV-1 entry. In addition, this molecule has been successfully crystallized as a complex with CD4 and an monoclonal antibody, 17b, and their structure solved at 2.5

Å by Hendrickson's group at Columbia University(9). It is, thus, possible to correlate the HIV-neutralization activity of an antibody to its epitope-binding specificity. To prepare the deglycosylated wtΔ protein, Dr. Kwong's experimental procedure is followed [(39)and Kwong & Hendrickson, personal communication].

Conjugation of the gp120 preparation to α(1→6)dextran will follow a procedure established by Dr. J. Mond's group [(40) and Dr. Andrew Lee, personal communication]. Briefly, aminoethyl-carbamylmethyl dextran (AECM-dextran) is prepared to have amino group introduced onto the neutral polysaccharide. The deglycosylated wtΔ protein of gp120 is then covalently linked through stable thioether bonds to AECM-dextran using a heteroligation technique. The protein will be lightly S-acetylthiolated and the dextran be acylated by introduction of iodoacetamido groups. The two components are then mixed in the presence of hydroxylamine which removes the S-acetyl group. The exposed free sulfhydryl reacts in situ with the iodoacetamido groups.

As evidenced by the anti-Ig-dextran conjugates prepared by the group, this method allows better preservation of protein native structure. Picogram quantities of anti-Ig antibodies coupled to α(1→6)dextran can induce profound B cell activation and antibody production (40). The effects of such conjugates on class switching of IgM to IgA, however, was not reported in their publications.

The quality of the gp120-dextran conjugates, i.e., their protein conformation and epitope expression, is monitored by ELISA using antibodies specific for various epitopes of gp120 antibodies. These specific reagents are obtainable from the AIDS Research and Reference Reagent Program or be commercially available. For ELISA assay, the conjugates are captured by anti-α(1→6)dextran mAb pre-coated on ELISA plates. The final evaluation of these conjugates will be of the immune responses they elicit.

b) Dex-LeY-peptide conjugate. This conjugate is designed to induce IgA antibodies specific for the exposed carbohydrate molecule attached on the gp120 glycoprotein of HIV-1. Masking of the neutralization epitopes of gp120 by glycosylation represents one of the important mechanisms that HIV-1 escapes from host immune responses. Recently, some unique carbohydrate structures were identified in the gp120 glycoprotein of HIV-1, such as Tn (GalNAc-Ser/Thr) and Lewis Y(Fucα1→2Gal β1→4 (Fucα1→3)GlcNAc β1→3Gal β1→4Glc β1→R), raising the possibility of developing vaccines using these structures. These epitopes appear a s surface antigens on most primary human breast carcinomas and their metastases (41), being also molecular targets for cancer vaccination(42, 43).

A DEX-LeY-peptide conjugate is made using a peptide (YYRYD) (SEQ. ID NO. 1) that mimics the carbohydrate structure of Lewis Y. The molecular and functional mimicry of the carbohydrate epitope by the peptide(YYRYD) (SEQ. ID NO. 1) was recently established by Dr. Thomas Kieber-Emmonslgroup(41). When mice were immunized with a proteosome complex of the peptide, HIV-1 neutralization antibodies were elicited in the serum of both C57BL and Balb/c. Whether the proteosome complex elicited IgA responses was not reported(41).

The Lewis Y-mimicking peptide will be coupled to α(1→6) dextran of proper M.W. For coupling with amino-dextran by glutaraldehyde-conjugation(44), a Lys r es id ue is added in the C-terminal of the peptide. The sequences resulted is "YYRYDK" (SEQ ID NO. 2). The number of the epitopes per carrier molecule can be controlled by varying the molar ratio of carrier:hapten during conjugation. The conformation of the Lewis Y-mimicking epitope in the conjugate can be investigated using anti-Lewis Y monoclonal antibody, BR552, by an ELISA method(See below).

An ELISA-based Method for Monitoring the Quality of a Conjugate

Basically, the conjugates are captured by anti-dextran mAb pre-coated on plate and the coupled antigen revealed by another specific antibody to the antigen: a. Coat ELISA plate with monoclonal anti-dextran, 45.21.1(α,K)(30, 45), at 5 mg/ml, in 0.1 M NaHCO3 pH9.6, 37° C., 2 hours; Wash the plates using ELISA washing solution(lXPBS, 0.05% Tween20, 0.025% NaAzide) and block with the same solution containing 1% BSA; b. Incubate the coated plates with serial dilution of the conjugate at 37° C. for 2 hours then wash them with ELISA washing solution; c. Incubate with antibodies specific for different epitopes of a given protein at 37° C. for 2 hours then wash them with ELISA washing solution; d. Incubate with a second antibody specific for the isotype of the anti-protein antibody used above to monitor the conjugated epitopes; in separate wells, apply an alkali phosphatase(AP)-labeled anti-dextran, such as 45.21.1-AP, to detect the available epitopes of the carrier.

This method allows for testing whether desired antigenic determinants are present in a conjugate and if they are in the native configurations that are recognizable by antibodies of defined specificities. The molar ratio of an antigen to a carrier in a conjugate by a semi-quantitative ELISA assay can also be estimated. In previous experiments, several Gag-DEX conjugates were tested and it was found that the immunochemical nature of a conjugate as measured by the ELISA assay correlates well with its in vivo induction of B cell responses.

Aim 3. Route(s) of Administration of TI-conjugates for the Induction of IgA

The route of antigen administration is one of the critical factors influencing the efficacy of a vaccination (2, 46). The mucosal immune response has certain regional nature, i.e., local exposure to an antigen can result in much higher levels of specific secretory IgA in the region of exposure than at distant sites. Recent studies showed further that immunization at a local site may selectively enhance the responses at other particular sites in addition to the original site. For example, when a TD-antigen cholera toxin(CT) was used to immunize mice, the rectal route was found to be able to induce specific IgA responses at both colonic-rectal and vaginal mucosal sites (47, 48). The basis of these phenomena is believed to be the selective homing of IgA-committed B cells to their functional sites, which are regulated by their differential expression of homing receptors, such as α4β7 (49).

In this experiment, TI-conjugates are studied. The nature of their B cell activation differs significantly from those elicited by a TD-antigenic stimulation. Whether the B cells activated by a T-independent antigen gain a mucosal homing phenotype is unknown. It is documented, however, that the spleen plays an important role in the TI-responses to microbial polysaccharides (50, 51). Thus, the systemic route of immunization when the DEX-conjugates are used must not ignored. Both systemic immunization and mucosal local vaccinations are to be studied.

For systemic immunization, normal C57BL and the TCR-KO mice are given a single dosage i.v. injection. For the mucosal vaccination, the colonic-rectal route is taken as described (47). This route was shown to be the best for induction of IgA responses at the colonic-rectal site as well as the vaginal site (47, 48). The dosage and time (kinetics) responses to each conjugate are studied. The B cell responses in spleen and gut tissues by tissue section staining and by ELISAspot assay as described (18) are monitored. Specific antibodies in serum and in gut secretions are detected by ELISA assay for their binding to gp120 and to the carrier molecule. Dr. Marian R. Neutra's wick method is adapted to collect mucosal secretions of the gut(47).

The following questions are specifically addressed:
1. Can TI-conjugates induce antigen-specific IgA-B cells in spleen as well as in the gut? The carrier molecule alone has been found to induce s-IgA in gut secretion in the TCR-KO mice (data not shown). These IgA antibodies may be derived from circulation via an active IgA-transporting system in the liver. Alternatively, they may be produced locally by IgA-plasma cells migrated (from spleen) to lamina propria of the gut. It is predicted that the first mechanism certainly contributes to s-IgA in the gut. The second mechanism is, however, not impossible, since i) the homing receptor $\alpha 4\beta 7$ is detectable in the peritoneal B-1 cells (52); ii) B-1 cells contribute to IgA-plasma cells in the gut (5, 6, 53); and iii) both B-1 and conventional B cells are involved in the splenic B cell responses to $\alpha(1\rightarrow 6)$dextran (34). If the number of antigen-specific IgA-plasma cells in the gut were significantly increased, either by a single i.v.-injection of an antigen or as a consequence of a local mucosal boosting with the antigen, the second possibility, i.e., a TI-antigen-induced B-cell migration and mucosal homing, will be strongly supported. Further studies in this direction will be carried.
2. Can these TI-conjugates elicit IgA-antibodies specific for the expected epitopes of the gp120 glycoprotein of HIV-1? At this stage, applicants use the glycosylated native gp120 and the deglycosylated gp120 wtΔ for ELISA to distinguish the specificities for protein-epitope-specificities and those for carbohydrate structures.
3. Can they elicit a booster response? As shown in FIG. 1 (progress report), the number of IgA-secreting cells in the spleen of normal mice is drastically less than those of IgM-anti-dextrans. This isotype profile differs from the previous observation that about equal number of IgA- and IgM-hybridoma were obtained from the mice immunized by $\alpha(1\rightarrow 6)$ dextran (19, 30). One hypothesis is that in the presence of function al T-cells(normal mice), the IgA-committed cells activated in the spleen migrate to the mucosal sites for their terminal differentiation and s-IgA production. In the absence of T-cells(TCR-KO), however, their terminal differentiation may take place in the spleen. To test this possibility, the immunized-mice are challenged via the rectal route of immunization. Both TCR-KO and normal mice are used in the experiments. If a booster-response in the gut is observed in normal mice but not in TCR-KO mice, this hypothesis will be supported.
4. Can the se TI-conjugates elicit gp120-specific germinal centers in spleen and gut? Answering this question is important, since many of the critical molecular and cellular events of B cell activation and differentiation take place in the germinal center, i ncludin g clonal selection and expansion of B memory cells, class switching, somatic hypermutation and affinity maturation. These TI-conjugates may be trapped by follicular dendritic cells via their binding to $\alpha(1\rightarrow 6)$dextran or by other mechanisms and thus are potentially capable of inducing germinal center reaction in normal mice.

If a gp120-specific IgA response cannot be effectively induced by these conjugates, the search for improvement in two direction is planned: i) Structure of conjugates. An important parameter that may be adjusted further is the molecular weight of the final product. The optimal molecular weights chosen for conjugation is based on a study in Aim1 using DEX-FITC as a model. Since FITC is a small hapten, the carrier M.W. required for DEX-FITC may differ from those for DEX-gp120 or DEX-LeY; ii) Different vaccination strategies. For example, mice may be primed with a TD-conjugate to initiate a B cell response and then boost them using above TI-conjugate. In AIDS patients, the antibody response to HIV protein was already initiated by the infection. Vaccination with the TI-conjugates for them may be sufficient to induce an IgA-response. Thus, boosting with TI-conjugates may be an important addition to HIV-therapeutic vaccinations.

Aim 4. HIV Neutralization Activity and Binding Specificities of IgA Antibodies a) Neutralization of HIV. It is of critical importance to test whether the IgA-antibodies induced by above TI-conjugates can neutralize various strains of HIV-1. Sera and gut secretions can be sufficient for an initial testing; a detailed characterization will be done using monoclonal antibodies (see below). Samples collected from immunized mice are compared with those from non-immunized animals.

The HIV neutralization assay is performed as described (41). Briefly, Cell-free HIV-1/MN and HIV-1/3B, obtainable from the AIDS Research and Reference Reagent Program, will be propagated in H9 cells. One hundred TCID50 of virus free of cells are pre-incubated with serial dilution of experimental samples for 1 hour at 37° C. The pretreated virus is then plated on target cells, for 1 h. Neutralization is detected as inhibition of syncytia 3 days later, assessed by counting the number of multinuclear cells. The neutralization activities using clinical isolates of HIV-1 will be tested further.

b) Monoclonl antibodies with interesting specificities for gp120. Several reasons make it necessary to establish specific monoclonal antibodies in this proposal:
1) To correlate the neutralization activity of an antibody to its epitope-binding specificity. As described above, the structures of gp120 wtΔ and its complex with CD4 and mAb 17b have been solved. A series of mutant clones of gp120 are also available, allowing detailed analysis of antibody binding specificities for the protein. Although a panel of monoclonal antibodies of defined anti-gp120 specificities have been established (11), it is of interest to obtain mAb recognizing other conserved, neutralization epitopes of gp120, including particularly those specific for the carbohydrate structure attached to gp120 glycoprotein. Since here a distinct strategy is developed, i.e., the TI-route of IgA induction, monoclonal antibodies of unique specificities may be obtained. There is much evidence that antibodies recognizing the exposed carbohydrate structures of microorganisms are frequently protective against infection by corresponding pathogens (2, 17). Such specificities can be especially important for protection against HIV-1 by mucosal IgA.
2) To test whether anti-gp120 mabs of IgA isotype are better than other antibody isotypes for HIV-1 neutralization and what kind of epitope-binding specificities can be better associated with the IgA-mediated neutralization activities. Monoclonal antibodies with same V-region but different H-chain isotypes, either IgA or IgG, are required for these studies.
3) To see whether our immunization strategy using TI-conjugates can induce IgA-antibodies of higher affinities and if somatic mutation occurs during the TI-route of IgA induction. For these purposes, immunochemical mapping and molecular characterization of antibody combining-site of monoclonal antibodies are necessary.

It is expected that hybridomas will be established in this project period. In fact, applicants must do so when a specific IgA response is monitored in a vaccination. Hybridoma techniques were applied in previous studies to obtain mAbs to dextrans and to other antigens (19, 30). These techniques are applied to obtain monoclonal antibodies with interesting specificities to the gp120 glycoprotein of HIV-1. To investigate the above questions monoclonal antibodies are to be used.

In summary, α(1→6)dextran, a newly discovered IgA-activator, is used as a carrier to present distinct antigenic determinants of the gp120 glycoprotein of HIV-1. Two T-independent conjugates, DEX-gp120 wtΔ and DEX-LeY-peptide, are produced and their efficacy in eliciting IgA-responses to HIV-1 investigated. Both T-cell deficient mice and normal C57BL are applied to study the immunological activities of these conjugates. Important information regarding vaccine development using α(1→6)dextran is provided. These studies, if successful, are extended to human vaccination against HIV-1.

REFERENCES FOR THE SECOND SERIES OF EXPERIMENTS

1. Mestecky, J., and J. R. McGhee. 1987. Immunoglobulin A (IgA): molecular and cellular interactions involved in IgA biosynthesis and immune response. [Review]. Advances in Immunology 40:153–245.
2. Kraehenbuhl, J. P., and M. R. Neutra. 1992. Molecular and cellular basis of immune protection of mucosal surfaces. Physiological Rev. 72:853–879.
3. Seilles, E., D. Vuitton, P. Sava, P. Claude, J. Panouse, A. Roche, and D. L. Delacroix. 1985. IgA and its different molecular forms in the mesenteric, portal and peripheral venous blood in man. Gastroenterol. Clin. Biol. 9:607–613.
4. Mestecky, J., C. Lue, and M. W. Russell. 1991. Selective transport of IgA: cellular and molecular aspects. Gastroenterol. Clin. North. Am. 20:441–471.
5. Bos, N. A., J. C. Bun, S. H. Popma, E. R. Cebra, G. J. Deenen, M. J. van der Cammen, F. G. Kroese, and J. J. Cebra. 1996. Monoclonal immunoglobulin A derived from peritoneal B cells is encoded by both germ line and somatically mutated VH genes and is reactive with commensal bacteria. Infection & Immunity 64:616–23.
6. Bos, N. A., J. C. Bun, H. Bijma, E. R. Cebra, J. J. Cebra, G. J. Deenen, M. J. van der Cammen, and F. G. Kroese. 1994. Analysis of IgA-producing hybridomas derived from peritoneal B1 cells. Advances in Experimental Medicine & Biology 355:265–9.
7. Varmus, H. E. 1983. Retroviruses. In Mobile Genetic Elements. J. A. Shapiro, ed. Academic Press, New York, p. 411–501.
8. Sabin, A. B. 1992. Improbability of effective vaccination against human immunodeficiency virus because of its intracellular transmission and rectal portal of entry. Proc. Natl. Acad. Sci. USA 89:8852–8855.
9. Kwong, P. D., R. Wyatt, J. Robinson, R. W. Sweet, J. Sodroski, and W. Hendrickson. 1998. Structure of an HIVgp120 envelope glycoprotein in complex with the CD4 receptor and a neutralizing human antibody. Nature 393:648–659.
10. Rizzuto, C. D., R. Wyatt, N. Hernandez-Ramos, Y. Sun, P. D. Kwong, W. Hendrickson, and J. Sodroski. 1998. A conserved HIVgp120 glycoprotein structure involved in chemokine receptor binding. Science 280:1949–1953.
11. Wyatt, R., P. D. Kwong, E. Desjardins, R. W. Sweet, J. Robinson, W. Hendrickson, and J. Sodroski. 1998. The antigenic structure of the HIVgp120 envelope glycoprotein. Nature 393:705–711.
12. Wei, X., S. K. Ghosh, M. E. Taylor, V. A. Johnson, E. A. Eminl, P. Deutsh, J. D. Lifson, S. Bonhoeffer, M. A. Nowak, B. H. Hahn, M. S. Saag, and G. M. Shaw. 1995. Viral dynamics in human immunodeficiency virus type 1 infection. Nature 373:117–122.
13. Ho, D. D., A. U. Neumann, A. S. Perelson, W. Chen, J. M. Leonard, and M. Markowitz. 1995. Rapid turnover of plasma virions and CD4 lymphocytes in HIV-1 infection. Nature 373:123–126.
14. Campbell, B. J., and V. M. Hirsch. 1994. Extensive envelope heterogeneity of simian immunodeficiency virus in tissues from infected macaques. J. Virol. 68:3129–3137.
15. Hirsch, V. M., J. E. Martin, G. Dapolito, W. R. Elkins, W. T. London, S. Goldstein, and P. R. Johnson. 1994. Spontaneous substitutions in the vicinity of the V3 analog affect cell tropism and pathogenicity of simian immunodeficiency virus. J. Virol. 68:2649–2661.
16. Mond, J. J., A. Lees, and C. M. Snapper. 1995. T cell-independent antigens type 2. In Annual Review of Immunology, vol. 13, p. 655–92.
17. Wang, D., and E. A. Kabat. 1996. Carbohydrate Antigens (Polysaccharides). In Structure of Antigens, vol. Three. M. H. V. V. Regenmortal, ed. CRC Press, Boca Raton New York London Tokyo, 1996., p. 247–276.
18. Wang, D., S. M. Wells, A. M. Stall, and E. A. Kabat. 1994. Reaction of germinal centers in the T-independent response to the bacterial polysaccharide α(1→6)dextran. Proc. Natl. Acad. Sci. USA 91:2504–2506.
19. Wang, D., J. Liao, D. Mitra, P. N. Akolkar, F. Gruezo, and E. A. Kabat. 1991. The repertoire of antibodies to a single antigenic determinant. Mol. Immunol. 28:1387–1397.
20. Mombaerts, P., E. Mizoguchi, H. G. Ljunggren, J. Iacomini, H. Ishikawa, L. Wang, M. J. Grusby, L. H. Glimcher, H. J. Winn, A. K. Bhan, and S. Tonegawa. 1994. Peripheral lymphoid development and function in T cell receptor mutant mice. Int. Immunol. 6:1061–1070.
21. Poussier, P., P. Edouard, C. Lee, M. Binnie, and M. Julius. 1992. Thymus-independent development and negative selection of T cells expressing T cell receptor a/b in the intestinal epithelium: evidence for distinct circulation patterns of gut- and thymus-derived T lymphocytes. J. Exp. Med. 176:187–199.
22. Saito, H., Y. Kanamori, T. Takemori, H. Nariuchi, E. Kubota, H. Takahashi-Iwanaga, T. Iwanaga, and H. Ishikawa. 1998. Generation of intestinal T cells from progenitors residing in gut cryptopatches. Science 280:275–278.
23. Franco, M. A., and H. B. Greenberg. 1997. Immunity to rotavirus in T cell deficient mice. Virology 238:169–179.
24. Jeanes, A. 1986. Immunochemical and related interactions with dextrans reviewed in terms of improved structural information. Mol. Immunol. 23:999–1028.
25. Sallusto, F., M. Cella, C. Danieli, and A. Lanzavecchia. 1995. Dendritic cells use macropinocytosis and the mannose receptor to concentrate macromolecules in the major histocompatibility complex class II compartment: downregulation by cytokines and bacterial products [see comments]. J Exp Med 182:389–400.
26. Kabat, E. A., and D. Berg. 1953. Dextran—an antigen in man. J.Immunol. 70:514–532.
27. Noorman, F., M. M. Barrett-Bergshoeff, M. Bekkers, J. J. Emeis, and D. C. Rijken. 1997. Inhibition of mannose receptor-mediated clearance of tissue-type plasminogen activator (t-PA) by dextran: a new explanation for its antithrombotic effect. Thromb Haemost 78:1249–54.

28. Schuler, W., A. Schuler, and E. Kolsch. 1984. Immune response against the T-independent antigen alpha (1 - - - 3) dextran. II. Occurrence of B gamma memory cells in the course of immunization with the native polysaccharide is T cell dependent. European Journal of Immunology 14:578–85.

29. Tittle, T. V. 1989. Immunochemical analyses of C57BL/6J monoclonal anti-α(1→3) Dextran antibodies. Mol. Immunol. 26:343–350.

30. Wang, D., H. Chen, J. Liao, P. N. Akolkar, S. K. Sikder, F. Gruezo, and E. A. Kabat. 1990. Two families of monoclonal antibodies to α(1→3)dextran, VH19.1.2 and VH9.14.7, show distinct patterns of Jk and JH minigene usage and amino acid substitutions in CDR3. J. Immunol. 145:3002–3010.

31. Herzenberg, L. A., A. M. Stall, P. A. Lalor, C. Sidman, W. A. Moore, D. R. Parks, and L. A. Herzenberg. 1986. The Ly-1 B cell lineage. Immunological Reviews 93:81–102.

32. Herzenberg, L. A., and A. B. Kantor. 1993. B-cell lineages exist in the mouse. [Review]. Immunology Today 14:79–83.

33. Forster, I., and K. Rajewsky. 1987. Expansion and functional activity of Ly-1+ B cells upon transfer of peritoneal cells into allotype-congenic, newborn mice. Eur. J. Immunol. 17:521–528.

34. Wells, S. M., D. Wang, E. A. Kabat, and A. M. Stall. 1998. Involvement of B-1 and Conventional B Cell Populations in the T-independent Response to α(1→6)dextran. J. Immunol.:Submitted.

35. Fernandez, C., and G. Moller. 1979. A thymus-independent IgG response against dextran B512 can be induced in C57BL but not in CBA mice, even though both strains possess a VHdex gene. Scand J Immunol 10:465–72.

36. Chen, H. T., S. D. Makover, and E. A. Kabat. 1987. Immunochemical studies on monoclonal antibodies to stearyl-isomaltotetraose from C58/J and a C57BL/10 nude mouse. Mol. Immunol. 24:333–338.

37. Matsuda, T., and E. A. Kabat. 1989. Variable region cDNA sequences and antigen binding specificity of mouse monoclonal antibodies to isomaltosyl oligosaccharides coupled to proteins T-dependent analogues of α(1→6) dextran. J. Immunol. 142:863–870.

38. Kabat, E. A., and A. E. Bezer. 1958. The effect of variation in molecular weight on the antigenicity of dextran in man. Arch. Biochem. Biophys. 78:306–318.

39. Kwong, P. D., R. Wyatt, J. Robinson, R. W. Sweet, J. Sodroski, and W. Hendrickson. 1998. Quantitative probability analysis and variational crystalization of gp120, the exterior envelope glycoprotein of the human immunodeficiency virus type 1(HIV-1). J. Biol. Chem. (submitted).

40. Brunswick, M., F. Finkelman, P. F. Highet, J. K. Inman, H. M. Dintzis, and J. J. Mond. 1988. Picogram quantities of anti-Ig antibodies coupled to dextran induce B cell proliferation. J. Immunol. 140:3364.

41. Agadjanyan, M., P. Luo, M. A. Westerink, L. A. Carey, W. Hutchins, Z. Steplewski, D. B. Weiner, and T. Kieber-Emmons. 1997. Peptide mimicry of carbohydrate epitopes on human immunodeficiency virus [see comments]. Nat Biotechnol 15:547–51.

42. Springer, G. F., P. R. Desai, W. Wise, S. C. Carlstedt, R. Stein, H. Tegtmeyer, and E. F. Scanlon. 1990. Pancarcinoma T and Tn epitopes: autoimmunogens and diagnostic markers that reveal incipient carcinomas and help establish prognosis. In Immunodiagnosis of Cancer. R. Herberman, and D. Mercer, eds. Marcel Dekker, New York, p. 587–612.

43. Barr, N., C. R. Taylor, T. Young, and G. F. Springer. 1989. Are pancarcinoma T and Tn differentiation antigens? (published erratum corrected in Cancer Oct 15, 1989;64(8):1594.). Cancer 64:834–841.

44. Avrameas, S. 1969. Coupling of enzyme to proteins with glutaraldehyde. Immunochemistry 6:42–52.

45. Sharon, J., E. A. Kabat, and S. M. Morrison. 1982. Immunochemical characterization of binding sites of hybridoma antibodies specific for α(1→6)linked dextran. Mol. Immunol. 19:375.

46. Mestecky, J. 1987. The common mucosal immune system and current strategies for induction of immune responses in external secretions. [Review]. Journal of Clinical Immunology 7:265–76.

47. Haneberg, B., D. Kendall, H. M. Amerongen, F. M. Apter, J. P. Kraehenbuhl, and M. R. Neutra. 1994. Induction of specific immunoglobulin A in the small intestine, colon-rectum, and vagina measured by a new method for collection of secretions from local mucosal surfaces. Infect Immun 62:15–23.

48. Haneberg, B., D. Kendall, H. M. Amerongen, F. M. Apter, and M. R. Neutra. 1995. The colon and rectum as inductor sites for local and distant mucosal immunity. Adv Exp Med Biol 371A:107–109.

49. Butcher, E. C., and L. J. Picker. 1996. Lymphocyte homing and homeostasis. Science 272:60–6.

50. Van den Eertwegh, A. J. M., J. Laman, D., M. M. Schellekens, W. J. A. Boersma, and E. Claassen. 1992. Complement-mediated follicular localization of T-independent type-2 antigens: the role of marginal zone macrophages revisited. Eur. J. Immunol. 22:719–726.

51. Timens, W., A. Boes, T. Rozeboom-Uiterwijk, and S. Poppema. 1989. Immaturity of the human splenic marginal zone in infancy: possible contribution to the deficient infant immune response. J. Immunol. 143:3200–3206.

52. Donze, H. H., C. Lue, B. A. Julian, W. H. Kutteh, A. Kantele, and J. Mestecky. 1997. Human peritoneal B-1 cells and the influence of continuous ambulatory peritoneal dialysis on peritoneal and peripheral blood mononuclear cell (PBMC) composition and immunoglobulin levels. Clin Exp Immunol 109:356–61.

53. Kroese, F. G., J. J. Cebra, J. F. van der Cammen, A. B. Kantor, and N. A. Bos. 1995. Contribution of B1 cells to intestinal IgA production in the mouse. Methods 8:37–43.

What is claimed is:

1. A method for inducing in a subject the production of IgA antibodies that specifically bind to an HIV-1 epitope, which method comprises administering to the subject a conjugate comprising an α(1,6)dextran moiety covalently bound to a protein moiety, wherein (i) the protein moiety has on its surface an HIV-1 epitope and (ii) the dextran moiety has a molecular weight of at least 90 kD, thereby inducing in the subject the production of IgA antibodies that specifically bind to an HIV-1 epitope.

2. The method of claim 1, wherein the HIV-1 epitope is present on gp120, Gag p55 or capsid p24.

3. The method of claim 1, wherein the HIV-1 epitope is present on a wild-type deglycosylated HIV-1 protein.

4. The method of claim 3, wherein the wild-type deglycosylated HIV-1 protein binds to CD4 or an HIV-1 co-receptor.

5. The method of claim 4, wherein the HIV-1 co-receptor is CCR5.

6. The method of claim 1, wherein the HIV-1 epitope is present on a deletion mutant of a deglycosylated wild-type HIV-1 gp120 glycoprotein.

7. The method of claim 6, wherein the deletion mutant does not possess domains $v_1$ and $v_2$ present in deglycosylated wild-type HIV-1 gp120 glycoprotein.

8. The method of claim 1, wherein the α(1,6) dextran moiety is bound to the protein moiety via heteroligation.

9. The method of claim 1, wherein the protein moiety is a glycoprotein and the HIV-1 epitope is present on the surface of the carbohydrate portion thereof.

10. The method of claim 1, wherein the protein and dextran moieties are bound to each other by avidin.

11. The method of claim 1, wherein the HIV-1 epitope on the protein's surface is Tn (GalNAc-Ser/Thr), Lewis Y (Fucα1→2Galβ1→4 (Fucα1→3) GlcNAcβ1→3Galβ1→4Glcβ1→R), or a peptide mimic thereof.

12. The method of claim 11, wherein the peptide mimic is selected from the group consisting of (i) a peptide mimic of Lewis Y; (ii) the peptide YPY; (iii) the peptide WRY; and (iv) a peptide having a mucin-type or a peripheral poly-N-acetyl-glucosamine carbohydrate structure.

13. The method of claim 12, wherein the peptide mimic of Lewis Y comprises the amino acid sequence YYRYD or YYRYDK.

14. The method of claim 1, wherein the protein moiety is a Gag-GST fusion protein.

15. The method of claim 1, wherein the conjugate is administered to the subject topically, orally, anally, intravenously or subcutaneously.

16. The method of claim 1, wherein the conjugate is administered to the subject via liposome or aerosol delivery.

17. The method of claim 16, wherein the conjugate is administered via a liposome.

18. The method of claim 17, wherein the liposome further comprises an isomaltosyl oligosaccharide incorporated therein.

19. The method of claim 18, wherein the isomaltosyl oligosaccharide comprises a $[Glc(α(1,6)]_n$ motif.

20. The method of claim 1, wherein the subject is infected with HIV-1.

21. The method of claim 1, wherein the subject is T-cell-deficient.

22. The method of claim 1, wherein the subject is not T-cell-deficient.

23. A method for determining the extent to which a conjugate comprising an α(1,6)dextran moiety covalently bound to a protein moiety stimulates the production of IgA antibodies that specifically bind to an HIV-1 epitope, the protein moiety having on its surface an HIV-1 epitope and the dextran moiety having a molecular weight of at least 90 kD, which method comprises the steps of:

(a) administering the conjugate to a subject under conditions permitting the production of IgA antibodies; and (b) after a period of time sufficient to permit the production of IgA antibodies, determining the amount of IgA antibodies produced by the subject that specifically bind to the HIV-1 epitope present on the protein moiety's surface, thereby determining the extent to which the conjugate stimulates the production of IgA antibodies that specifically bind to an HIV-1 epitope.

24. The method of claim 23, wherein the HIV-1 epitope is present on gp120, Gag p55 or capsid p24.

25. The method of claim 23, wherein the HIV-1 epitope is present on a wild-type deglycosylated HIV-1 protein.

26. The method of claim 25, wherein the wild-type deglycosylated HIV-1 protein binds to CD4 or an HIV-1 co-receptor.

27. The method of claim 26, wherein the HIV-1 co-receptor is CCR5.

28. The method of claim 23, wherein the HIV-1 epitope is present on a deletion mutant of a deglycosylated wild-type HIV-1 gp120 glycoprotein.

29. The method of claim 28, wherein the deletion mutant does not possess domains $v_1$ and $v_2$ present in deglycosylated wild-type HIV-1 gp120 glycoprotein.

30. The method of claim 23, wherein the $\alpha(1,6)$ dextran moiety is bound to the protein moiety via heteroligation.

31. The method of claim 23, wherein the protein moiety is a glycoprotein and the HIV-1 epitope is present on the surface of the carbohydrate portion thereof.

32. The method of claim 23, wherein the protein and dextran moieties are bound to each other by avidin.

33. The method of claim 23, wherein the HIV-1 epitope on the protein's surface is Tn (GalNAc-Ser/Thr), Lewis Y (Fuc$\alpha$1$\rightarrow$2Gal$\beta$1$\rightarrow$4(Fuc$\alpha$1$\rightarrow$3) GlcNAc$\beta$1$\rightarrow$3Gal$\beta$1$\rightarrow$4Glc$\beta$1$\rightarrow$R), or a peptide mimic thereof.

34. The method of claim 33, wherein the peptide mimic is selected from the group consisting of (i) a peptide mimic of Lewis Y; (ii) the peptide YPY; (iii) the peptide WRY; and (iv) a peptide having a mucin-type or a peripheral poly-N-acetyl-glucosamine carbohydrate structure.

35. The method of claim 34, wherein the peptide mimic of Lewis Y comprises the amino acid sequence YYRYD or YYRYDK.

36. The method of claim 23, wherein the protein moiety is a Gag-GST fusion protein.

37. The method of claim 23, wherein the conjugate is administered to the subject topically, orally, anally, intravenously or subcutaneously.

38. The method of claim 23, wherein the conjugate is administered to the subject via liposome or aerosol delivery.

39. The method of claim 38, wherein the conjugate is administered via a liposome.

40. The method of claim 39, wherein the liposome further comprises an isomaltosyl oligosaccharide incorporated therein.

41. The method of claim 40, wherein the isomaltosyl oligosaccharide comprises a $[Glc(\alpha(1,6)]_n$ motif.

* * * * *

SEQUENCE LISTING

```
<160> NUMBER OF SEQ ID NOS:   2

<210> SEQ ID NO 1
<211> LENGTH: 5
<212> TYPE: PRT
<213> ORGANISM: unknown
<220> FEATURE:
```

```
-continued

<221> NAME/KEY: PEPTIDE
<222> LOCATION: (1)..(5)
<223> OTHER INFORMATION: mimics the carbohydrate structure of Lewis Y.

<400> SEQUENCE: 1

Tyr Tyr Arg Tyr Asp
1               5

<210> SEQ ID NO 2
<211> LENGTH: 6
<212> TYPE: PRT
<213> ORGANISM: unknown
<220> FEATURE:
<221> NAME/KEY: PEPTIDE
<222> LOCATION: (1)..(6)
<223> OTHER INFORMATION: mimics the carbohydrate structure of Lewis Y.

<400> SEQUENCE: 2

Tyr Tyr Arg Tyr Asp Lys
1               5
```